(12) United States Patent
McEachern et al.

(10) Patent No.: US 6,307,067 B1
(45) Date of Patent: Oct. 23, 2001

(54) PALLADIUM AND BORON CO-CATALYZED ADDITION OF OXYGEN NUCLEOPHILES TO VINYL EPOXIDES

(75) Inventors: Ernest John McEachern, White Rock; Francisco Dean Toste, Mississauga, both of (CA); Barry Martin Trost, Los Altos Hills, CA (US)

(73) Assignee: The Board of Trustees of the Leland Stanford Junior University

( * ) Notice: Subject to any disclaimer, the term of this patent is extended or adjusted under 35 U.S.C. 154(b) by 0 days.

(21) Appl. No.: 09/390,828

(22) Filed: Sep. 7, 1999

Related U.S. Application Data

(60) Provisional application No. 60/099,505, filed on Sep. 9, 1998, and provisional application No. 60/105,868, filed on Oct. 27, 1998.

(51) Int. Cl.$^7$ .................. C07D 317/12; C07C 209/00; C07C 41/02
(52) U.S. Cl. .............. 549/296; 549/378; 549/346; 549/427; 549/497; 564/487; 564/413; 568/675; 568/662; 568/857
(58) Field of Search .................. 549/296, 378, 549/346, 427, 497; 564/487, 413; 568/675, 662, 857

(56) References Cited

U.S. PATENT DOCUMENTS

| | | | |
|---|---|---|---|
| 5,739,396 | 4/1998 | Trost et al. | 564/15 |
| 5,919,948 | 7/1999 | Trost et al. | 548/478 |

OTHER PUBLICATIONS

Trost et al., Palladium–Mediated Vicinal Cleavage . . . A Cis Hydroxylation Equivalent, Oct. 1985, J. Am. Chem. Soc., vol. 107, pp. 6123–6124.*

Trost et al., An Asymmetric Synthesis of Vigabatrin, Dec. 1996, Tetrahedron Letters, vol. 37, No. 51, pp. 9161–9164.*

Trost et al., Catalyst Controlled Diastereoselective N–Alkylation of alpha–Amino Esters, Mar. 1998, Tetrahedron Letters, vol. 39, pp. 1713–1716.*

International Search Report for Application No. GB99/02973.

Trost, B.M., "An asymmetric synthesis of vigabatrin." Tetrahedron Letter 37(51): 9161–9164 (Dec. 1996).

Trost, B.M., "Catalyst controlled diasteeoselective N–alkylation of alpha–amino esters." Tetrahedron Letters 39(13): 1713–1716 (1998).

Trost, B.M., "On ligand design for catalytic outer sphere reactions: a simple asymmetric synthesis of vinylglycinol." Angewante Chemie International Edition 35(1): 99–102 (1996).

Trost, B.M., "Tin mediated palladium catalyzed regiocontrolled alkylations of vinyl epoxides." Tetrahedron Letters 29(24): 2931–2934 (1988).

Trost, B.M., "Palladium–mediated vicinal cleavage of allyl epoxides with retention of stereochemistry: a cis hydroxylation equivalent." Journal of the American Chemical Society 107(21): 6123–6124 (1985).

Trost, B.M., "A two–component catalyst system for asymmetric allylic alkylations with alcohol pronucleophiles." Journal of the American Chemical Society 120(48) : 12702–12703 (1998).

* cited by examiner

*Primary Examiner*—Rosalynd Keys
(74) *Attorney, Agent, or Firm*—LeeAnn Gorthey

(57) ABSTRACT

Nucleophilic oxygen species, such as primary alcohols, carboxylates, and water, are added to vinyl epoxides in a highly regioselective and enantioselective manner, providing a convenient route to enantiomerically enriched 1,2-diols and oxygen-containing heterocycles. The reaction employs a chiral Pd(0) complex and a borane or borate as co-catalysts Also described are similar additions of nitrogen nucleophiles, and the addition of carbonates to vinyl epoxides using a chiral Pd(0) catalyst.

31 Claims, 2 Drawing Sheets

PALLADIUM AND BORON CO-CATALYZED ADDITION OF OXYGEN NUCLEOPHILES TO VINYL EPOXIDES

This application claims priority to U.S. provisional applications 60/099,505, filed on Sep. 9, 1998, and 60/105,868, filed Oct. 27, 1998, which are hereby incorporated by reference in their entirety.

This invention was made with Government support under contract CHE-9501472 by the National Science Foundation and contract GM33049 awarded by the National Institute of Health. Accordingly, the U.S. Government has certain rights in the invention.

FIELD OF THE INVENTION

The present invention relates to a catalytic method for use in highly regioselective and enantioselective additions of oxygen nucleophiles to vinyl epoxide substrates. The reaction employs a chiral Pd complex and a boron co-catalyst. Also described are additions of nitrogen nucleophiles, and related addition reactions of oxygen nucleophiles employing only the chiral Pd catalyst.

REFERENCES

Boudreau, C. et al., U.S. Pat. No. 5,574,186(1996).
Bunt, R. C., Ph.D. Thesis, Stanford University, 1996, p. 252.
Collman, J. P. et al., Science 26:1404 (1993).
Guibe, F., Saint M'Leux, Tetrahedron Leu. 1981, 22, 3591.
Jacobsen, E. N. et al., J. Am. Chem. Soc. 112:2801 (1990).
Jacobsen, E. N. et al., Science 277(5328):936–938 (1997a).
Jacobsen, E. N. et al., U.S. Pat. No. 5,665,890 (1997b).
Katsuki, T. and Sharpless, K. B., U.S. Pat. No. 4,471,130 (1984).
Lakamiri, R., Lhoste, P., and Sinou, D,. Tetrahedron Lett. 1989, 30, 4669.
Lakhmiri, R., Lhoste, P., and Sinou, D., Synth. Commun. 1990a, 20, 1551.
Lakhmiri, R., Lhoste, P., Boullanger, P., and Sinou, D., J. Chem. Res. (S), 1990b, 342.
Saigo, K. et al., Bull. Chem. Soc. Japan 59(3):931 (1986).
Singaram, B. et al., U.S. Pat. No. 5,367,073 (1994).
Sinou, D. et al., Tetrahedron Lett. 1995, 36, 251.
Trost, B. M. and Tenaglia, A., Tetrahedron Len. 1988, 29, 2931.
Trost, B. M., Ito, N., and Greenspan, P. D., Tetrahedron Lett. 1993, 34, 1421.
Ukai, T. et al., J. Organometal. Chem 1974, 65, 253.

BACKGROUND OF THE INVENTION

A long-standing challenge in palladiumn π-allyl chemistry has been the use of oxygen nucleophiles to generate O-allylated species with good regio- and enantioselectivity (FIG. 1A). Although phenols and carboxylates have been shown to be good nucleophilic partners for this type of reaction, alcohols have generally given poor results due to their sluggish reactivity and moderate regioselectivity.

Only a few literature examples employing alcohols as nucleophiles with Pd π-allyls have appeared, most of which involve simple O-allylation of alcohols (Lakhmiri et al., 1989), in which neither regio- nor stereoselectivity is an issue (Guibe et al, Lakhmiri et al., 1990$a$, 1990$b$). Several examples of Pd(0)-catalyzed O-glycosylation of sugars to produce 1,4-disaccharides have been reported by Sinou et al.

Trost et al have investigated a number of strategies for the delivery of oxygen nucleophiles (or hydroxyl equivalents) to Pd π-allyl complexes arising from vinyl epoxides. Specifically, Trost and Tenaglia (1988) examined the use of alkoxystannanes for the regioselective 1,2-addition of alkoxy groups to vinyl epoxides. The reaction was not stereoselective, and its scope of this reaction was somewhat limited in that good yields were obtained only by the use of cyclic stannylene diethers.

As part of a total synthesis of zoapatanol, Trost and Ito (1993) developed the use of triphenylsilanol as a water surrogate that selectively adds in a 1,4sense to vinyl epoxides. The products of this reaction were formed mainly with the E-geometry. However, attempts to repeat this work using a chiral ligand (Bunt, 1996) were unsuccessful.

A general method for regio- and enantioselective addition of alcohols to vinyl epoxides, therefore, has not yet been reported. Such a procedure would be extremely valuable in the preparation of chiral precursor molecules to biologically important molecules, or as building blocks for chiral reagents for use in synthesis, optical resolution, etc. In particular, the enantioselective addition of a hydroxyl equivalent (more precisely, a water equivalent) to a vinyl epoxide would generate the vinylglycidol in enantiopure form. The latter chemistry would provide a facile route to two commercially important chiral pool molecules and, as such, would be competitive with the Jacobsen procedure (i.e. kinetic resolution of the corresponding epoxides; Jacobsen, 1997$a$) for generation of these materials.

SUMMARY OF THE INVENTION

In one aspect, the invention provides a method of selectively adding a nucleophilic species, preferably a nucleophilic oxygen species, to a vinylic epoxide. The vinylic epoxide is contacted with a borane or borate reagent, in the presence of said nucleophilic species and a chiral catalytic Pd complex, thereby forming an addition product, preferably an O-allyl product, which is enriched in one of the possible stereoisomeric products of such an addition. The nucleophilic oxygen species is preferably a primary alcohol, water, an acetate, a carbonate, or a bicarbonate.

In a preferred procedure for carrying out the reaction, the nucleophilic species and chiral catalytic Pd complex are combined, prior to or concomitant with contacting the vinylic epoxide and boron reagent, in a substantially oxygen-free atmosphere in a solvent selected from dichloromethane, 1,2-dichloroethane, tetrahydrofuran, and diethyl ether. Dichloromethane is a particularly preferred solvent. The concentration of the vinylic epoxide in the reaction mixture is preferably less than 1.0M, more preferably less than 0.5M, and most preferably about 0.1 to 0.25M, although lower concentrations may be used.

The borane or borate reagent preferably comprises boron substituted with three groups independently selected from alkyl, alkoxy, aryl, aryloxy, aralkyl, aralkyloxy, alkylamino, arylamino, aralkyl, aralkylamino, hydroxy, or oxide. Preferred species are trialkylboranes, dialkylalkoxyboranes, dialkoxyalkylboranes, or trialkyl borates, where the alkyl or alkoxy substituents may be further substituted with aryl. Particularly preferred are those represented by $BR_3$, $BR_2OR'$, $BR(OR')_2$, or $B(OR)_3$, where R and R' are independently $C_1$ to $C_4$ alkyl or benzyl. Of these, preferred compounds are $Et_3B$, $s$-$Bu_3B$, $n$-$Bu_3B$, $Et_2BOMe$, $B(OiPr)_3$, $B(OtBu)_3$, and $B(OBz)_3$.

The chiral catalytic Pd complex is typically formed in situ from (i) a Pd(0) species, or a Pd(II) species effective to be reduced to a Pd(0) species, and (ii) a chiral ligand effective to form the complex by reaction with the Pd(0) species. The chiral catalytic Pd complex includes a chiral ligand, where the ligand preferably comprises (i) a chiral component derived from a chiral diamine, diol, amino alcohol, or dicarboxylic acid, this component having first and second chiral centers, each substituted with a group X selected from oxygen, nitrogen, or a carbonyl group, and, (ii) linked to each group X, a binding component, comprising a sterically bulky group effective to complex with the central palladium atom. Preferably, this group is a phosphine-containing group, and most preferably a (diarylphosphino)aryl group, such as 2-(diphenylphosphino)benzene or 2-(diphenylphosphino) naphthalene. In preferred ligands, each of the binding components, which need not be identical, is linked to a chiral center of the chiral component via a carboxylic amide or carboxylic ester linkage.

The chiral centers are connected by a direct bond, or by a chain of one to three atoms comprising linkages selected from alkyl, alkenyl, ailyl ether, alkyl amino, or a combination thereof. Preferably, the chiral component is derived from a chiral diamine, and more preferably a chiral 1,2-diamine, such as enantiomerically enriched trans-1,2-cyclohexyldiamine, trans-1,2-diamino-1,2-diphenylethane, or dibenzo-2,3-diamino[2.2.2]bicyclooctane. In particularly preferred ligands, a (diarylphosphino)aryl group, such as those named above, is linked to a chiral center of said chiral component via a 1-amido linkage.

In a preferred embodiment of the method, the vinylic epoxide is a terminal epoxide, having no further substitution at the epoxy carbons, such as butadiene monoepoxide.

In one aspect, the addition is regioselective, in that the nucleophilic species adds predominantly at the epoxy carbon of said epoxide bearing the vinylic group, giving predominantly a 1,2-addition product. Preferably, no significant amount of the 1,4-addition product is produced. The addition is also enantioselective, and produces an addition product having an enantiomeric excess preferably greater than 75%, more preferably greater than 85%, and most preferably greater than 95%.

In one embodiment of the method, useful for producing enantiomerically enriched 1,2-diols, the nucleophilic oxygen species is water, an acetate, a carbonate, or a bicarbonate. When the oxygen species is an acetate, carbonate, or bicarbonate, the contacting of the reagents takes place in the presence of water. Preferably, a phase transfer catalyst is employed.

In another embodiment of the invention, useful for the preparation of enantiomerically enriched ribose and deoxyribose precursors, the nucleophilic oxygen species is a primary allylic alcohol, and the product of the addition is thereby a vinyl allyl ether. In this embodiment, the method further comprises subjecting the vinyl allyl ether to an olefin metathesis reaction, which is effective to generate an enantiomerically enriched 2,5-dihydrofuran having one or two substituents at the 2 position. Also provided is the preparation of homologous vinyl alkenyl ethers, via the addition of homologous alkenyl alcohols, which may be cyclized to larger oxygen heterocycles.

In a related embodiment, the nucleophilic species is a nitrogen nucleophile, such as an alkyl or aralkyl amine. In a specific embodiment, the nucleophilic species is a primary alkyl amine.

In a related aspect, the invention provides a method of selectively adding carbonate to a vinylic epoxide. The vinylic epoxide is contacted, in a chlorocarbon solvent, with a carbonate, a bicarbonate, or carbon dioxide, in the presence of a chiral catalytic Pd complex and water, thereby forming a cyclic carbonate product which is enriched in one of the possible stereoisomeric products of such an addition. Preferably, a phase transfer catalyst is also present. The preferred solvent is dichloromethane. In a preferred embodiment, the vinylic epoxide is a terminal epoxide, having no further substitution at the epoxy carbons, such as butadiene monoepoxide. Preferred chiral catalytic Pd complexes are as described above. As above, the catalyst is typically formed in situ from (i) a Pd(0) species, or a Pd(II) species effective to be reduced to a Pd(0) species, and (ii) a chiral ligand effective to form said complex by reaction with the Pd(0) species.

DETAILED DESCRIPTION OF THE INVENTION

I. Definitions

Figure 1A:
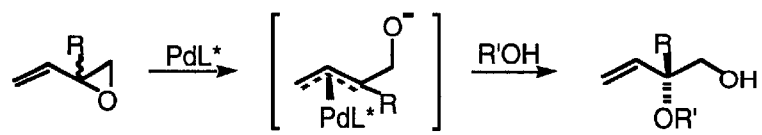
FIGS. 1A and 1B illustrate the addition of an oxygen nucleophile to a vinyl epoxide via a palladium π-allyl complex, and a proposed mechanism for the boron-mediated reaction.

The terms below have the following meanings unless indicated otherwise. "Enantiomeric excess" or "e.e." refers to the quantity E1–E2, where E1 is the fraction of a compound having one enantiomeric configuration, and E2 is the fraction having the mirror image configuration.

An "enantioselective" addition reaction refers to an addition reaction which produces one possible enantiomer of the center to which the nucleophile adds in excess over the other enantiomer. The product of such an addition is referred to as "enantiomerically enriched" or "optically active."

A "chiral ligand", as used herein, indicates an asymmetric ligand which is enantiomerically pure or enantiomerically enriched. Typically, the ligand is asymmetric by virtue of first and second asymmetrically substituted carbon atoms. A chiral catalyst as described herein, comprising a chiral ligand, is effective to catalyze an addition reaction as described herein such that an enantiomerically enriched addition product is obtained from a starting material having an achiral or racemic carbon at the site of the addition. Preferably, the addition product has an e.e., as defined above, which is greater than 70%, more preferably greater than 85%, and most preferably greater than 95%.

A "chiral component", as used herein in reference to chiral ligands used in the catalysts of the invention, refers to a chiral diol, diamino, amino alcohol or dicarboxyl moiety which forms a chiral scaffold to which two binding groups, as defined herein, are linked.

"Alkyl" refers to a fully saturated acyclic monovalent radical containing carbon and hydrogen, and which may be branched or a straight chain. Examples of alkyl groups are methyl, ethyl, n-butyl, t-butyl, n-heptyl, and isopropyl. "Cycloalkyl" refers to a fully saturated cyclic monovalent radical containing carbon and hydrogen, which may be further substituted with alkyl. Examples are cycloalkyl groups are cyclopropyl, methyl cyclopropyl, cyclobutyl, cyclopentyl, ethylcyclopentyl, and cyclohexyl.

"Lower alkyl" refers to an alkyl radical of one to six carbon atoms, as exemplified by methyl, ethyl, n-butyl, i-butyl, t-butyl, isoamyl, n-pentyl, and isopentyl.

"Aryl" refers to a substituted or unsubstituted monovalent aromatic radical having a single ring (e.g., phenyl) or two or more condensed rings (e.g., naphthyl, phenanthryl, anthracyl). Other examples include heterocyclic aromatic ring groups having one or more nitrogen, oxygen, or sulfur atoms in the ring, such as furyl, pyrrole, pyridyl, and indole. "Aralkyl" refers to an alkyl, preferably lower alkyl, substituent which is further substituted with an aryl group; one example is a benzyl group.

II. Stereoselective Addition of Oxygen Nucleophiles

In accordance with one aspect of the invention, a method is provided for selectively adding a nucleophilic oxygen species to a vinylic epoxide, giving an O-allyl product which is enriched in one of the possible stereoisomeric products of the addition The addition is regioselective, giving a preponderance of 1,4 addition product over 1,2 addition product. In fact, in the majority of reactions, no 1,4 addition product is detected. The reaction is also enantioselective, giving e.e.'s over 70%, preferably over 85%, and more preferably over 95%.

Figure 1B:
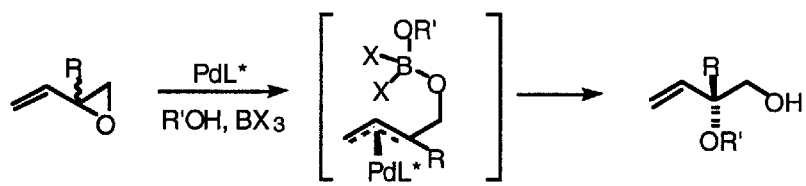

In carrying out the reaction, the substrate, which is a vinylic epoxide or a molecule including such a structure, is contacted with a borane or borate reagent in the presence of a nucleophilic oxygen species and a chiral catalytic Pd complex. According to a proposed mechanism (FIG. 1B), a π-allyl complex is formed between the chiral Pd catalyst (represented by PdL*) and substrate, and the complex undergoes an equilibrating deracemization, which accounts for the stereoselectivity of the addition reaction. Subsequently (or in competition with the racemization), a boron-nucleophile complex becomes coordinated to the former epoxy oxygen, and the nucleophile adds to the π-allyl complex. However, it is not intended for the scope of the invention to be bound or limited in any way by the proposed mechanism.

Suitable and preferred reagents and conditions for the reaction are discussed in the following sections.

A. Boron Reagent

The boron reagent is a borane or borate, comprising boron substituted with three groups independently selected from alkyl, alkoxy, aryl, aryloxy, aralkyl, aralkyloxy, alkylamino, arylamino, aralkyl, aralkylamino, hydroxy, or oxide (as in $B_2O_3$). Preferably, the substituents are selected from alkyl, alkoxy, aryl, aryloxy, aralkyl, and aralkyloxy. These substituents are effective to exchange with nucleophilic oxygen species, e.g. ROH, to form an intermediate complex with the oxygen nucleophile and the substrate.

A variety of different boron sources were examined for their efficacy in the reaction shown below, in which benzyl alcohol is added to isoprene monoepoxide, 1. The model reaction employs a chiral catalyst formed in situ from $Pd_2dba_3 \cdot CHCl_3$ and a chiral ligand, as described further below.

The results of this study are shown in Table I. All reactions were conducted on a 0.25 mmol scale in $CH_2Cl_2$, using 1.0 equiv. $PhCH_2OH$, 1% Pd and 3% ligand (based on mole percent relative to subtrate). The times indicated are the times for which each reaction was allowed to run, which in most cases was longer than the time required for the reaction to progress to completion. Except where indicated, all yields reported herein are estimated yield based on crude $^1H$ NMR spectra, TLC data, and GC traces of product mixtures. In Table 1, entry 10 reports an isolated yield.

TABLE I

Effect of Different Boron Sources on e.e.

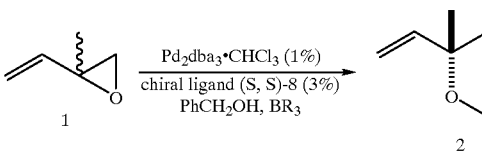

| Entry | Boron Source | Conc. | Rxn Temp | Rxn Time | Yield | e.e. |
|---|---|---|---|---|---|---|
| 1 | 1% $B(OCH_2Ph)_3$ | 0.1M | r.t. | 3 h | ~85% | 80% |
| 2 | 1% $B(OMe)_3$ | 0.1M | r.t. | 3 days | ~10% | — |
| 3 | 5% $B_2O_3$ | 0.5M | r.t. | 18 h | ~70% | 40% |
| 4 | 5% $B_2O_3$ | 0.1M | r.t. | 18 h | ~50% | 65% |
| 5 | 1% $PhB(OH)_2$ | 0.1M | r.t. | 18 h | ~30% | 50% |
| 6 | 1% $Et_2BOMe$ (1M, THF) | 0.1M | r.t. | 18 h | ~70% | 92% |
| 7 | 1% B—MeO-9-BBN (1M, hexanes) | 0.1M | r.t. | 18 h | ~50% | 75% |
| 8 | 5% (R)-alpine-borane (0.5M, TMF) | 0.1M | r.t. | 18 h | ~60% | 77% |
| 9 | 1% $^nBu_3B$ (1M, $Et_2O$) | 0.1M | r.t. | 18 h | ~70% | 83% |
| 10 | 1% $Et_3B$ (1M, THF) | 0.1M | r.t. | 3 h | 93% | 94% |
| 11 | 1% $Et_3B$ (1M, THF) | 0.1M | 40° C. | 3 h | ~90% | 94% |

For reaction, reagents having alkyl or alkoxy substituents were generally more effective than boric oxide and boronic acid derivatives (i.e. $BR_2OH$ or $BR(OH)_2$; entries 3–5). Tribenzylborate and diethylmethoxyborane, for example, gave good yield and high e.e. (entries 1 and 6). The sterically bulky reagents B-MeO9-BBN and (R)-alpine-borane actually gave lower e.e.'s (entries 7–8); this finding suggests that for high enantioselectivity to be obtained, the boron catalyst may have to be sufficiently compact to fit into the chiral pocket of the Pd ligand. —With respect to trialkylboranes, $Et_3B$ gave better results than n-$Bu_3B$ in this reaction (entries 9–11) s-$Bu_3B$, not shown in Table I, proved particularly useful in addition to the less hindered substrate, butadiene monoepoxide (3, below).

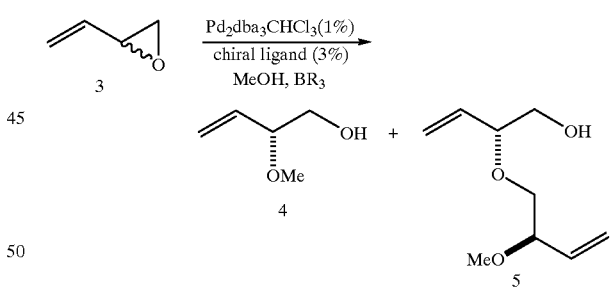

Boron reagents having more varied substituents were also employed in this reaction. For example, triethanolamine borate gave 4 in moderate yield and e.e. (60% and 58%, respectively), although substantial amount of dimeric product 5 was also formed.

In general, the preferred borane or borate reagent is a trialkylborane, dialkylalkoxyborane, dialkoxyalkylborane, or trialkyl borate, where the alkyl or alkoxy substituents may be further subsituted with aryl. More preferably, the reagent is $BR_3$, $BR_2OR'$, $BR(OR')_2$, or $B(OR)_3$, where R is $C_1$ to $C_4$ alkyl or benzyl; and, of these, $Et_3B$, s-$Bu_3B$, n-$Bu_3B$, $Et_2BOMe$, $B(OtBu)_3$ and $B(OBz)_3$ are generally preferred.

It should also be noted that in none of the above reactions was any of the 1,4-addition product detected, indicating that the boron catalyst exerts a strong regiodirecting effect.

The effect of varying the amount of boron reagents was also investigated, using the model reaction shown for Table I above. Unless otherwise stated, all reactions were conducted at room temperature on a 0.25 mmol scale, using 1.0 equiv. MeOH and 1.0 equiv. PhCH$_2$OH. Times indicated are times for which each reaction was allowed to run, although, in most cases, reactions were complete after 3 h. Results are given in Table II.

The results show that catalytic amounts of reagent were generally preferably to stoichiometric amounts (e.g., entries 1 vs. 2 and 5 vs. 6). A possible explanation for this effect is that deracemizing equilibration of the Pd-π-allyl complex (which is responsible for enantioselectivity) is believed to occur prior to complexation with boron; consequently, a high level of boron may compete with this equilibration. The effect of varying the amount of boron reagent at catalytic levels (1% to 10%) was also examined using a representative reagent, tribenzyl borate. It was observed that enantioselectivity decreased as the amount of tribenzyl borate used increased.

Trialkyl borane reagents (BR$_3$) were also found to produce higher e.e.'s than trialkyl borates (B(OR)$_3$) (entries 2 vs. 6 and 8 vs. 9).

representative ligand, the amine, alcohol, or carbonyl moieties, represented by groups X and X', are linked to first and second chiral centers, respectively, represented by starred carbon atoms. In preferred embodiments, the chiral centers are connected by a direct bond, represented by A in FIG. 2; that is, the diamine, diol, amino alcohol or dicarboxylic acid is a 1,2 system. However, chiral components having intervening bonds between the chiral centers, e.g. 1,3-, 1,4-, or 1,5- systems, have proven effective in the present reactions (data not shown). In such cases, group A connecting the chiral centers is a chain of one to three atoms comprising linkages selected from alkyl (carbon-carbon) alkyl ether (carbon-oxygen), alkyl amino (carbon-nitrogen), or a combination thereof. Examples of compounds based on chiral diols and diamines of this type are shown, for example, in Trost & Van Vranken, 1992.

Each of the chiral centers is further substituted with groups R$^1$ and R$^2$, respectively. These groups may be the same or different. The groups may be separate substituents, independently selected from aryl, heteroaryl, aralkyl, cycloalkyl, or heterocyclyl. Examples include, but are not limited to, phenyl, pyridyl, benzyl, naphthyl, cycloalkyl, furanyl, and pyranyl. Preferably, R$_1$ =R$^2$ R$^1$ and R$^2$ may also together form a carbocyclic or heterocyclic ring. Preferably, they form a 5- to 7- membered

TABLE II

Effect of Variation in Type and Quantity of Boron Reagent

| Entry | % Pd | Ligand | Boron Source | ROH | Conc. | Time | Product | Yield | e.e. |
|---|---|---|---|---|---|---|---|---|---|
| 1 | 0.1 | 0.3% (S,S)-8 | 100% B(OMe)$_3$ | none added | 0.5M | 18 h | 6 | ~80% | 2% |
| 2 | 1 | 3% (S,S)-8 | 1% B(OMe)$_3$ | MeOH | 0.1M | 3 h | 6 | ~80% | 49% |
| 3 | 1 | 3% (S,S)-8 | 100% Et$_2$BOMe | none added | 0.1M | 18 h | 6 | ~30% | 58% |
| 4 | 1 | 3% (S,S)-8 | 1% Et$_2$BOMe | MeOH | 0.1M | 18 h | 6 | ~80% | 90% |
| 5 | 1 | 3% (S,S)-8 | 100% Et$_3$B | MeOH | 0.1M | 18 h | 6 | ~70% | 60% |
| 7 | 1 | 3% (S,S)-8 | 1% Et$_3$B | MeOH | 0.1M | 3 h | 6 | 88% | 94% |
| 8 | 1 | 3% (S,S)-8 | 100% B(OCH$_2$Ph)$_3$ | none added | 0.5M | 3 h | 2 | ~80% | 31% |
| 8 | 1 | 3% (S,S)-8 | 5% B(OCH$_2$Ph)$_3$ | BzOH | 0.5M | 3 h | 2 | ~80% | 51% |
| 9 | 1 | 3% (S,S)-8 | 1% Et$_3$B | BzOH | 0.1M | 3 h | 2 | 93%$^e$ | 94% |

B. Palladium Catalyst

The nucleophilic addition reaction is carried out in the presence of a chiral catalytic Pd complex, effective to form a π-allyl complex with the vinyl epoxide. The catalytic complex comprises a chiral ligand complexed to palladium. Many such chiral ligands and complexes are known in the art, and it is expected that a wide range of such ligands will be useful in the present reaction.

In general, the chiral ligand can be viewed in terms of structural components, termed herein a chiral component and two binding components.

B1. Chiral Ligand: Chiral Component

Figure 2:
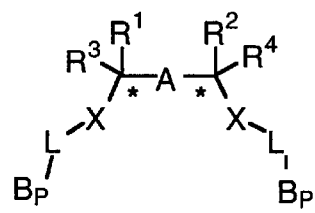
FIG. 2 shows the generic structure of a representative chiral ligand as used in the present reactions.

The chiral component is preferably derived from derived from a chiral diamine, diol, amino alcohol, or dicarboxylic acid. In FIG. 2, which shows the generic structure of a carbocyclic ring, or a 5- to 7-membered heterocyclic ring having 3 to 6 carbon ring atoms, with the remaining ring atoms selected from oxygen and nitrogen. Preferably, the heterocyclic ring contains one or two heteroatoms. Examples include, but are not limited to, piperidine, piperazine, pyrrolidine, morpholine, di- or tetrahydrofuran, and di- or tetrahydropyran. In all cases, R$^1$ and R$^2$, or the ring formed thereby, may be unsubstituted, or it may be have one or more substituents, such as alkyl, alkenyl, aryl, aralkyl, alkoxy, aryloxy, acyl, acyloxy, amide, tertiary amine, nitro, or halogen. Other types of substituents may also be present, although groups which are likely to act as nucleophiles in an allylic alkylation are less desirable, as they could be alkylated by the substrate under the reaction conditions. Such groups include primary and secondary amines and thiols. Phosphines are also less desirable substituents are they are likely to compete with binding group phosphines.

Additional rings may be fused to a ring formed by $R^1$ and $R^2$. $R^1$ and $R^2$, or the ring formed thereby, may also be fused to one or more additional rings.

As shown in structure I, the chiral centers also have substituents $R^3$ and $R^4$ to provide tetravalent carbon. Although $R^3$ and $^4$ are typically hydrogen, chiral components with tetrasubstituted chiral centers may also be used.

A distinctive type of chiral ligand, also suitable for use in the present catalysts, is that in which $R^1$ and $R^2$ are naphthyl groups which are linked to form a 1,1'-binaphthyl system (or analogous multinuclear systems). In such cases, for use in the present catalysts, the amine and/or alcohol groups of the chiral component are at the 2 and 2'-positions. Although these positions are not chiral centers in the conventional sense (i.e. they do not have four different substituents), the naphthyl groups form a helical system possessing what is termed axial chirality.

Preferred chiral components are derived from chiral 1,2-diamines. Of this group, those in which $R^1$ and $R^2$ form a ring are preferred. A particularly preferred chiral diamine of this class is 1R,2R-trans-diaminocyclohexane or its enantiomer, 1S,2S-trans-diaminocyclohexane (see FIG. 3, ligands 8 and 9), both of which are commercially available. Other preferred diamines include trans-1,2-diamino-1,2-diphenylethane and dibenzo-2,3-diamino-[2.2.2]bicyclooctane (see FIG. 3, ligands 10 and 11, respectively).

Many other chiral diamines, diols, and amino alcohols are commercially available. Such compounds can also be prepared from naturally occurring chiral precursors, e.g. amino acids, saccharides, tartrates, etc., using established synthetic procedures.

Chiral compounds may also be prepared from achiral or racemic precursors using known synthetic methods having high stereoselectivity. The development of such methods has been an active field of research for many years and is the subject of many articles, books and treatises. Well known examples which are particularly useful for preparation of the present ligands include the asymmetric epoxidation of allylic alcohols (Katsuki and Sharpless) and other olefins (e.g. Jacobsen 1990; Collman, 1993). Such epoxides can easily be converted to chiral 1,2diols or amino alcohols by ring opening with an appropriate nucleophile, e.g., azide followed by hydrogenation to give the amino alcohol. Hydroboration of enamines has been used to produce chiral β-amino alcohols (Singaram, 1994). Other reactions that could be useful in preparing the present ligands include the stereoselective reduction of bis-imines and keto oximes (Boudreau, 1996) and the enantioselective ring opening of epoxides and other labile rings (Jacobsen, 1997b).

In many cases, particularly for compounds which can form crystalline salts, e.g. many amines, optical resolution can provide compounds of high optical purity. For example, optical resolution of racemic 1,2-diphenylethanediamine gave the (+) and (−) enantiomers in over 99% and 97% optical purity, respectively (Saigo et al., 1986), and racemic trans-1,2-diaminocyclohexane was resolved to >99% optical purity via the lactic acid salt (Imaoka, 1995). Chromatography of racemic compounds on chiral supports has also been found useful.

B2. Chiral Ligand: Binding Components

As stated above, each chiral center of the chiral ligand is linked to a binding component. More precisely, each group X (oxygen, nitrogen or carbonyl) at each chiral center is linked to such a group, either directly, or more typically, via a linking functionality, represented as L in FIG. 2. For example, the group X will frequently form part of an amide or ester linkage to the binding component. Thus, the combined moiety —X—L—preferably represents —O—(C=O)—, —NR—(C=O)—, —(C=O)—O—, or —(C=O)—NR—, where R is lower alkyl or, preferably, hydrogen.

The binding component is a sterically bulky group effective to complex with the central palladium atom, preferably a phosphine-containing group. Phosphines and tertiary amines are groups which have such complexing capability and are not sufficiently nucleophilic to interfere with the addition reaction. Phosphines are preferred ligands for the present reactions. (Diarylphosphino)aryl binding groups have been found particularly effective; of these, most preferable are 2-(diphenylphosphino)benzoyl and 2-(diphenylphosphino)naphthoyl (see FIG. 3).

The naphthalene-based binding group of ligand 9 was found to give higher e.e.'s than the less bulky benzene-based group of ligand 8, particularly in reactions with less hindered and thus less discriminating substrates, such as butadiene monoepoxide. Adding additional steric bulk at the phenyl groups linked to phosphorus, however, did not appear to improve selectivity.

Figure 3:
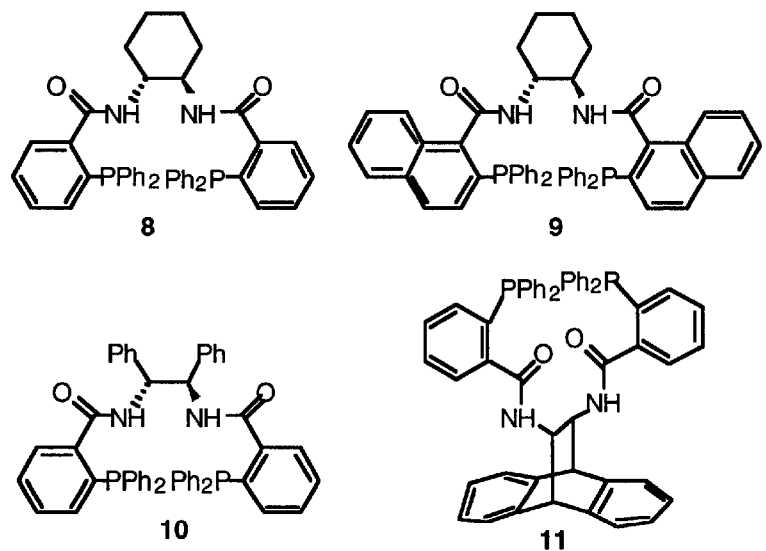
FIG. 3 show a selection of specific chiral ligands.

As shown in FIG. 3, the binding groups in these ligands are linked to the chiral component via 1-amido linkages. Ligands having the reverse amide structure, prepared from the corresponding chiral 1,2-dicarboxylic acids and 2-diphenylphosphinoaniline, were also effective, but generally less so than the structures illustrated in the Figure.

B3. Preparation of Catalyst

A convenient procedure for carrying out the reaction employs formation of the chiral catalytic Pd complex in situ from a soluble Pd(0) complex, or a soluble Pd(II) complex which can be converted to Pd(0) under the reaction conditions, and a chiral ligand. As described in Example 1, according to a preferred procedure, the Pd complex, ligand, and nucleophilic oxygen species are combined, the mixture is purged to remove oxygen, and solvent is added. The chiral catalyst is thus generated by ligand exchange of the chiral ligand with the Pd(0) complex. Suitable Pd(0) complexes are those having ligands which stabilize the starting complex, but are displacable by the chiral ligand. A generally useful starting complex is tris(dibenzylideneacetone) dipalladium(chloroform) ($Pd_2dba_3$-$CHCl_3$), which may be prepared according to the method described by Ukai et al.

Pd(II) complexes which are converted to Pd(0) under the reaction conditions can also be used to generate the catalyst. Useful examples are allylpalladium chloride dimer, palladium (II) acetate, and palladium (II) chloride. These compounds are reduced by species such as olefins, phosphines, and tertiary amines. A reducing agent such as butyl lithium or DIBAL (diisobutyl aluminum hydride) can also be added to facilitate the reaction.

A moderate excess of ligand over the stoichiometric (1:1) ratio of ligand to Pd is typically used in the formation of such complexes. Ratios from about 1:1 up to 3:1 were found to give good results; increasing the ratio to 6:1 had little effect. Using still higher amounts of ligand could be detrimental, in that the ligand could begin to coordinate to the metal in a monodentate, rather than bidentate, manner.

Increasing % Pd from 1% to 2% had no apparent beneficial effect on yield or selectivity. Lower levels of Pd were also found effective. The effect of the amount of Pd and chiral ligand used is discussed further in Section D, below.

C. Substrate

The substrate is a vinyl epoxide or a larger molecule containing such a structure. If competing functionalities, i.e. those expected to be nucleophilic under the reaction conditions, such as primary alcohols, primary or secondary amines, or thiols, are present in a larger structure, they are preferably masked, using protection strategies well known in the art, prior to the reaction.

Additions to substrates which are unsubstituted at the epoxy carbon(s) are likely to be less sterically discriminating, and thus give lower e.e.'s, than similar reactions of substituted substrates. The less hindered product is also more susceptible to dimerization reactions. As shown in Table III, however, e.e.'s greater than 85%, and monomer:dimer (4:5) ratios up to 98:2, were obtained in additions to butadiene monoepoxide using appropriate combinations of chiral catalyst and boron reagent. All reactions were conducted in $CH_2Cl_2$ using 1.0 equiv. MeOH, and times shown are times required for the reactions to progress to completion.

equiv. ROH, 1% Pd, and 3% chiral ligand 9. Reactions were generally complete in less than 18h.

It was found, for this series, that the naphthoyl ligand 9 generally gave better enantioselectivity than the benzoyl ligand 8 and, in most cases, s-$Bu_3B$ gave higher e.e. values than $Et_3B$. Particularly noteworthy is the highly enantioselective addition of 2-trimethylsilylethanol (entry 6); this reaction effectively represents a synthesis of the correspond-

TABLE III

Addition of Methanol to Butadiene Monoepoxide

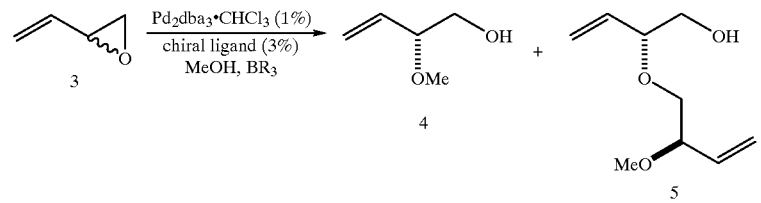

| Entry | % Pd | Ligand | Boron Source | Conc. | Temp | Time | Ratio 4:5 | Yield | e.e. |
|---|---|---|---|---|---|---|---|---|---|
| 1 | 1 | 3% (S,S)-9 | 1% $Et_3B$ (1M, THF) | 0.1M | 40° C. | 18 h | 69:31 | ~60% | 84% |
| 2 | 0.1 | 0.3% (S,S)-9 | 10% $Et_3B$ (1M, THF) | 0.1M | r.t. | 18 h | 91:9 | ~85% | 26% |
| 3 | 1 | 3% (S,S)-9 | 1% $^sBu_3B$ (1M, $Et_2O$) | 0.1M | r.t. | 18 h | 85:15 | ~80% | 89% |
| 4 | 1 | 3% (S,S)-9 | 1% $^sBu_3B$ (1M, $Et_2O$) | 0.1M | 40° C. | 3 h | 95:5 | ~80% | 84% |
| 5 | 0.5 | 1.5% (S,S)-9 | 1% $^sBu_3B$ (1M, $Et_2O$) | 0.1M | 40° C. | 3 h | 79:21 | ~60% | 82% |
| 6 | 0.5 | 1.5% (S,S)-9 | 2% $^sBu_3B$ (1M, $Et_2O$) | 0.1M | r.t. | 18 h | 98:2 | ~90% | 87% |

Table IV, below, shows the results of addition of several different alcohols to butadiene monoepoxide, generally with excellent regio- and enantioselectivity. Yields shown are isolated yields. Unless otherwise indicated, all reactions were conducted on a 0.25 mmol scale in $CH_2Cl_2$, using 1.0 ing diol in enantiopure form. The addition of p-methoxybenzyl alcohol (entry 7) is also synthetically equivalent to a preparation of the diol, as this protected alcohols can be readily converted to the corresponding benzylidene acetal by DDQ oxidation.

TABLE IV

Addition of Alcohols to Butadiene Monoepoxide

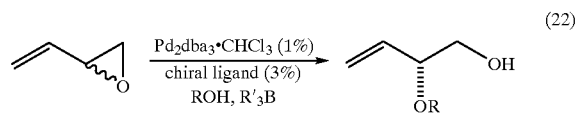

(22)

| Entry | $R'_3B$ | ROH | Temp | Time | Product | Yield | e.e. |
|---|---|---|---|---|---|---|---|
| 1 | 1% $Et_3B$ | MeOH | 40° C. | 18 h | 4 | ~70% | 84% |
| 2 | 1% $^sBu_3B$ | MeOH | r.t. | 3 h | 4 | ~70% | 89% |

TABLE IV-continued
Addition of Alcohols to Butadiene Monoepoxide (22)

| Entry | R'₃B | ROH | Temp | Time | Product | Yield | e.e. |
|---|---|---|---|---|---|---|---|
| 3 | 1% Et₃B | Allyl alcohol | r.t. | 18 h | 7 | ~80% | 87% |
| 4 | 1% ˢBu₃B | Allyl alcohol | r.t. | 18 h | 7 | ~80% | 92% |
| 5 | 1% ˢBu₃B | Propargyl alcohol | r.t. | 5 h | | 78% | 88% |
| 6 | 1% Et₃B | 2-(Trimethylsilyl ethanol | r.t. | 18 h | | 85% | 94% |
| 7 | 1% ˢBu₃B | 4-Methoxybenzyl alcohol | r.t. | 3 h | | 76% | 84% |
| 8[a] | 1% Et₃B | 4-Methoxybenzyl alcohol | 40° C. | 3 h | | 82% | 91% |

[a]Reaction was carried out in THF containing 5% DMAP using freshly distilled butadiene monoepoxide; yield is isolated yield.

Further addition reactions to butadiene monoepoxide, giving yields of about 75–85% and e.e.'s of about 85–95%, are described below, in Sections D (Table VI), E2 (Table VIII, entry 12), and E (Table IX, entry 4). As noted above, these reactions provide useful routes to enantiomerically enriched vinyl glycidols, either directly or via a 2-protected intermediate.

Cyclic substrates and more sterically hindered substrates may also be used. For example, benzyl alcohol was added to 1,3-cyclohexadiene monoepoxide, using 1% Pd₂dba₃.CHCl₃, 3% ligand 8 (racemic), 1% Et₃B, and 1.0 eq alcohol in CH₂Cl₂(40° C., 18h). This reaction gave a 60% yield of the trans-1,2-addition product, showing high regioselectivity and trans selectivity. Addition to a phenyl-substituted substrate, 2-phenyl-2-vinyl oxirane, was also investigated; the products of such additions could be useful as synthetic precursors to tachykinin receptor antagonists. For this reaction, the best results were obtained using a stoichiometric amount of tribenzyl borate or a pinacol derivative, 2-methoxy4,4,5,5, -tetramethyl-[1,3,2] dioxaborolane. Using 1 equivalent of the latter reagent, 1% Pd₂dba₃ CHCl₃, 3% (S,S)-8, and 5% DMAP in THF at room temperature for 18 h, a 72% yield of the methanol adduct, having 91% e.e., was obtained (see Example 9). Addition of benzyl alcohol under similar conditions, using 1 equivalent of tribenzyl borate, gave the adduct in about 60% yield and 84% e.e. (Example 10). It is hypothesized that stabilization of the borate ester intermediate by the adjacent phenyl ring may be responsible for low boron turnover in these reactions.

D. Reaction Conditions

In a typical procedure (see e.g. Example 1), the Pd catalyst, or, more typically, a Pd(0) complex and chiral ligand, as described above, are placed in an oven-dried vessel. The nucleophilic oxygen species (e.g. an alcohol) is preferably added at this point as well. The system is purged with an inert gas, preferably argon, to remove any traces of oxygen, and an oxygen-free solvent is then added. The solvent is an aprotic solvent, preferably a chlorinated solvent, and most preferably dichloromethane. Diethyl ether and THF were also found to be suitable solvents. The amount of solvent is preferably that required to give a 0.1M concentration of substrate, to be added later.

The chiral Pd catalyst is thus generated in situ upon addition of the solvent. As this mixture is agitated, a solution of the boron catalyst, preferably in dry, oxygen-free ether or THF, is added. A 1.0 M solution of the boron catalyst was generally used in the reactions described herein, but this concentration is not believed to be critical. To the resulting solution was added the substrate. The oxygen nucleophile and substrate are generally used in equimolar amounts, though excess alcohol may be used. The use of excess alcohol is desirable in the case of sluggish nucleophiles. In such cases, addition of DMAP (dimethylaminopyridine) can shown in Table V. Unless otherwise stated, all reactions were conducted at room temperature on a 0.25 mmol scale using 1.0 equiv. MeOH. Reactions were allowed to run for 18h; in most cases, reactions were complete after 3 h. Product ratios are based on GC analyses of product mixtures; entry 1 reports an isolated yield.

TABLE V

Optimization of Reaction Conditions for Large-Scale Preparation of 6

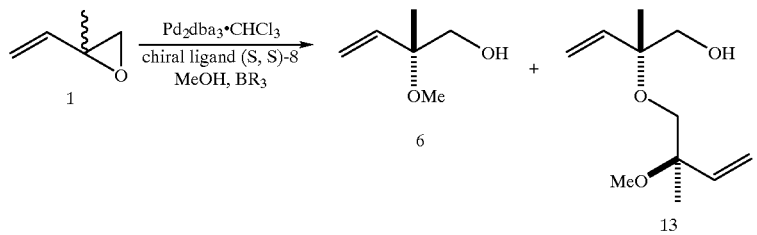

| Entry | % Pd | % (S,S)-8 | Boron Source | Solvent | Conc. | Ratio 6:13 | Yield | e.e. |
|---|---|---|---|---|---|---|---|---|
| 1  | 1    | 3    | 1% Et$_3$B     | CH$_2$Cl$_2$ | 0.1M  | 95:5  | 88%  | 94% |
| 2  | 0.1  | 0.3  | 1% Et$_3$B     | CH$_2$Cl$_2$ | 1M    | 67:33 | ~65% | 53% |
| 3  | 0.1  | 0.3  | 1.33% Et$_3$B  | CH$_2$Cl$_2$ | 0.75M | 95:5  | ~90% | 70% |
| 4  | 0.1  | 0.3  | 4% Et$_3$B     | CH$_2$Cl$_2$ | 0.25M | 97:3  | ~90% | 79% |
| 5  | 0.25 | 0.75 | 4% Et$_3$B     | CH$_2$Cl$_2$ | 0.1M  | 96:4  | ~80% | 88% |
| 6  | 0.5  | 1.5  | 2% Et$_3$B     | CH$_2$Cl$_2$ | 0.1M  | 96:4  | ~90% | 92% |
| 7  | 0.5  | 1.5  | 1% Et$_3$B     | CH$_2$Cl$_2$ | 0.2M  | 95:5  | ~85% | 88% |
| 8  | 1    | 3    | 0.5% Et$_3$B   | CH$_2$Cl$_2$ | 0.1M  | 93:6  | ~70% | 93% |
| 9  | 1    | 3    | 1% Et$_2$BOMe  | CH$_2$Cl$_2$ | 0.1M  | 94:6  | ~80% | 90% |
| 10 | 0.1  | 0.3  | 2% Et$_3$B     | THF          | 0.5M  | 90:10 | ~85% | 71% |
| 11 | 1    | 3    | 1% Et$_3$B     | THF          | 0.1M  | 90:10 | ~80% | 81% | also be beneficial; see, for example, the addition of acetol to isoprene monoepoxide, described in Section G3 below.

The substrate is then added to the reaction mixture. Liquid substrates, such as isoprene monoepoxide and butadiene monoepoxide, are most convenient added neat. For solid substrates, the substrate is dissolved in a minimal amount of a suitable oxygen-free solvent, preferably THF, ether, or dichloromethane.

The concentration of substrate in the final reaction solution is preferably less than 1.0 M, more preferably less than 0.5 M, and most preferably about 0.1M to 0.25 M. (It should be noted that the solvent added in the first stage of the reaction, preferably dichloromethane, generally makes up most of the volume of the final solution, and thus the concentration of substrate with respect to this solvent is close to its overall concentration in the reaction mixture.) An optimal concentration in terms of yield, selectivity and practical considerations was found to be about 0.1M. Reaction trends suggest that still lower concentrations would give good results, but these would be less practical on a larger scale.

When the reaction was run using preferred conditions of solvent, reagents, and substrate concentration, it was found that increasing the temperature of the reaction above room temperature generally did not appreciably improve yield or selectivity. However, in certain conditions, such as higher substrate concentrations (e.g. 0.5M), or the addition of bicarbonate in the presence of a phase transfer catalyst and water, described below, increasing the temperature moderately, e.g. to about 40° C., did give improved results. Further increases, however, were generally not productive.

The effect of varying % Pd, % boron, and solvent was examined for the model system shown below. The results are When the reaction was carried out using 0.1% Pd catalyst, varying % Et$_3$B and substrate concentration (entries 2–4), it was found that higher substrate concentrations gave lower e.e. values. More promising results were obtained by holding the substrate concentration at 0.1 M and varying % Pd and % Et$_3$B (entries 1, 5–6). However, carrying out the reaction with 0.5% Pd and 1% Et$_3$B at a slightly higher substrate concentration (0.2 M) also gave good yield and e.e. (entry 7).

It appears that yield and e.e. are not seriously impacted when smaller amounts of Pd are used in conjunction with larger amounts of Et$_3$B. It was noted, however, that the presence of trace oxygen in the solvent was more damaging at low levels of Pd. Using a higher amount of Pd and less Et$_3$B also gave high e.e. and adequate yield (entry 8), although these conditions would not be advantageous for large-scale synthesis.

Using THF as solvent with Et$_3$B as the boron source produced acceptable results, though e.e. values were somewhat lower and the formation of dimeric product was slightly increased (entries 10–11), in comparison to reactions run in dichloromethane.

Thus, the conditions best suited to carrying out this transformation on larger scale appear to be at a substrate concentration of 0.1–0.25 M, using 0.25–0.5% Pd and a corresponding amount of Et$_3$B (entries 8–10). In this sense, "corresponding" means that the product (% Pd) x (% B) x (substrate concentration) =0.1. As shown in the Table, however, moderate variations in the levels of catalysts gave good results.

The effect of varying solvent and amount and type of trialkyl boron catalyst was examined for the addition of p-methoxy benzyl alcohol to butadiene monoepoxide, using a chiral catalyst generated in situ from Pd$_2$dba$_3$.CHCl$_3$ and ligand 8 or 9. All reactions were conducted on a 0.25 mmol scale using 1.0 equiv. p-MeO-benzyl alcohol. Reactions were allowed to run for 18 h but were generally complete after 3 h. Results are shown in Table VI.

As shown, levels of catalysts could be varied to some degree without impairing the results, and use of 1,2-dichloroethane as a solvent gave results comparable to dichloromethane.

bicarbonates, also have significant utility, as discussed further below. The addition of primary alcohols was found to be a very versatile reaction, proceeding with good yields and very high regio- and enantioselectivity, as shown in Table VI. Reactions with secondary or tertiary alcohols, however, did not proceed under conditions found to be favorable for primary alcohols (i.e. 1% Pd complex, 3% chiral ligand, and 1% $Et_3B$ in dichloromethane at room temperature). The reactions shown in Table VI were conducted in $CH_2Cl_2$, using 1% $Pd_2(dba)_3 \cdot CHCl_3$, 3% (S,S)-8 as the chiral ligand, 1.0 equiv. isoprene monoepoxide, and 1.0 equiv. ROH. Times reported are those required for reactions to progress to completion, and yields are generally isolated yields.

TABLE VI

Variation of Reaction Conditions for Preparation of 12

| entry | % Pd | ligand | boron source | solvent | temp. | yield | e.e. |
|---|---|---|---|---|---|---|---|
| 1 | 1 | 3% (S,S)-9 | 1% $Et_3B$ (1M, THF) | $CH_2Cl_2$ | r.t. | ~65% | 84% |
| 2 | 1 | 3% (S,S)-9 | 1% $^sBu_3B$ (1M, $Et_2O$) | $CH_2Cl_2$ | r.t. | ~65% | 84% |
| 3 | 0.5 | 1.5% (S,S)-9 | 2% $Et_3B$ (1M, THF) | $Cl(CH_2)_2Cl$ | r.t. | ~70% | 82% |
| 4 | 0.5 | 1.5% (S,S)-8 | 2% $Et_3B$ (1M, THF) | $Cl(CH_2)_2Cl$ | 60° C. | ~70% | 85% |
| 5 | 1 | 3% (S,S)-9 | 1% $Et_3B$ (1M, THF) | $CH_2Cl_2$ | r.t. | ~70% | 83% |

E. Nucleophilic Oxygen Species

E1. Alcohols

The nucleophilic oxygen species is typically an alcohol, although water may be added directly, and reactions of carboxylate species, such as acetates, carbonates, and

TABLE VII

Addition of Alcohols to Isoprene Monoepoxide

| Entry | $R'_3B$ | ROH | Temp | Time | Product | Yield | e.e. |
|---|---|---|---|---|---|---|---|
| 1 | 1% $Et_3B$ | MeOH | r.t. | 3 h | 6 | 88% | 94% |
| 2 | 1% $Et_3B$ | Allyl alcohol | r.t. | 3 h | 14 | 83% | 95% |
| 3 | 1% $Et_3B$ | 2-(trimethylsilyl) ethanol | r.t. | 18 h | | ~60% | 98% |
| 4 | 1% $Et_3B$ | 2-(trimethylsilyl) ethanol | 40° C. | 4 h | | ~60% | 98 |
| 5 | 1% $Et_3B$ | 3-hydroxy propionitrile | r.t. | 18 h | | ~80% | 81% |
| 6 | 1% $^sBu_3B$ | 3-hydroxy propionitrile | 40° C. | 4 h | | 81% | 90% |

TABLE VII-continued

Addition of Alcohols to Isoprene Monoepoxide

| Entry | R'₃B | ROH | Temp | Time | Product | Yield | e.e. |
|---|---|---|---|---|---|---|---|
| 7 | 1% Et₃B | 4-hydroxy-2-butanone | r.t. | 3 h | | 83% | 93% |
| 8 | 1% Et₃B | 1,3-butanediol | r.t. | 3 h | | 87% | 85% |
| 9 | 1% ⁿBu₃B | 1,3-butanediol | r.t. | 5 h | | 80% | 98% |
| 10 | 1% Et₃B | Benzyl alcohol | r.t. | 3 h | 2 | 93% | 94% |
| 11 | 1% Et₃B | 4-Methoxybenzyl alcohol | r.t. | 3 h | | 91% | 94% |
| 12 | 1% Et₃B | Phenol | r.t. | 0.5 h | | 44% | 14% |

A wide variety of functionality is tolerated in the primary alcohol, including alkenes, trialkylsilyl groups, nitriles, ketones, secondary alcohols, and aryl groups (entries 1–11). The chemoselectivity observed for 1,3-butanediol is notable; none of the adduct arising from addition of the secondary alcohol was observed (entries 8–9).

The addition of phenol (entry 12) proceeded in good yield, but with low enantioselectivity. This may be due to the fact that phenol is an excellent nucleophile, and thus adds rapidly to the Pd π-allyl complex, before deracemization can take place.

E2. Hydroxyl Equivalents and Water

The effective addition of HOH to a vinyl epoxide provides a route to enantiomerically enriched 1,2-diols. Section F1, below, describes how this conversion may be accomplished by addition of a substituent (such as those shown in Table VII) which can subsequently be converted to a hydroxyl group. This route is especially useful in generating selectively protected diols (see Section F2, below). However, a one-step preparation of such diols is also desirable.

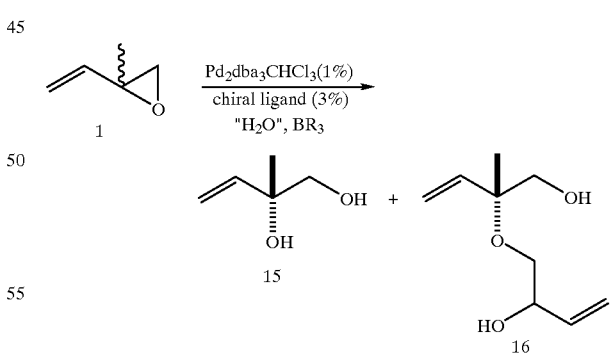

Reaction with NaOAc, using Et₃B as the boron catalyst, gave a roughly 1:1 mixture of diol and dimer. It is expected that addition of an acid source, such as HOAc, to the reaction, would protonate the initial diol product and disfavor formation of dimeric material.

An effective system employs a carbonate or bicarbonate as the nucleophile, in the presence of water and, optionally, a phase transfer catalyst, such as tetrabutylammonium chloride. Other phase transfer catalysts, e.g. other quaternary ammonium salts, quaternary phosphonium salts, and cryptands such as crown ethers, all of which are well known in the art, may also be used.

All reactions shown in Table VIII were conducted on a 0.25 mmol scale in $CH_2Cl_2$ at 0.1 M using 1.0 equiv. $NaHCO_3$ and 1% $Et_3B$ (see Example 11A). Reactions were allowed to run for 18 h, and generally required at least 8h for completion. The addition of a small amount of water was found to facilitate this reaction and give somewhat better yields when using the racemic ligand (entries 1–2). It was also found that increasing the reaction temperature from room temperature to 40° C. increased both the yield and the enantioselectivity (entries 3 and 7), even in the absence of $Bu_4NCl$ (entry 8). This reaction was repeated on a preparative scale (entry 9), yielding the diol 15 in 91% isolated yield and 97% e.e. Finally, use of $Na_2CO_3$ as a nucleophile (entries 10–11; see Example 11B) gave results essentially identical to those obtained using $NaHCO_3$. Sodium and lithium carbonates gave similar results; larger counterions (potassium and cesium) gave slower reactions and lower yields, though e.e.'s were similar.

The reaction could also be carried out using an excess of water (entries 6 and 12; see Example 11C). In the addition to butadiene monoepoxide (entry 12), the reaction was carried out in a two-phase system of water and dichloromethane, and give 70–80% yields of vinyl glycidol having about 90% e.e. It was also found that the reaction proceeds well using $H_2O$ alone as the nucleophile, giving a 75% yield of the diol in 93% e.e. after 3 hours at room temperature.

TABLE VIII $Et_3B$-Catalyzed Addition of $NaHCO_3$ or $Na_2CO_3$ to Vinyl Epoxides

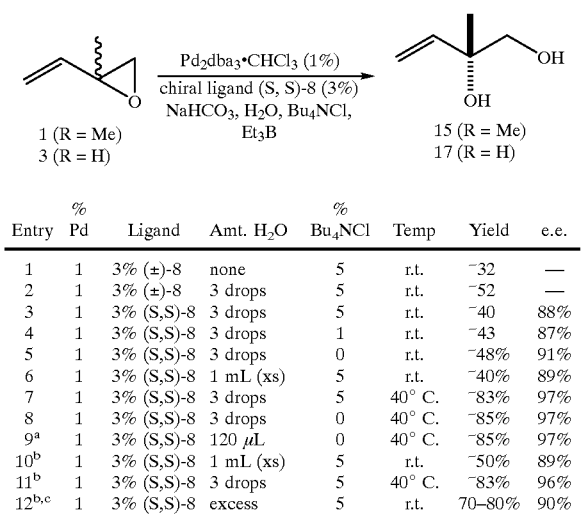

1 (R = Me)
3 (R = H)

15 (R = Me)
17 (R = H)

| Entry | % Pd | Ligand | Amt. $H_2O$ | % $Bu_4NCl$ | Temp | Yield | e.e. |
|---|---|---|---|---|---|---|---|
| 1 | 1 | 3% (±)-8 | none | 5 | r.t. | ~32 | — |
| 2 | 1 | 3% (±)-8 | 3 drops | 5 | r.t. | ~52 | — |
| 3 | 1 | 3% (S,S)-8 | 3 drops | 5 | r.t. | ~40 | 88% |
| 4 | 1 | 3% (S,S)-8 | 3 drops | 1 | r.t. | ~43 | 87% |
| 5 | 1 | 3% (S,S)-8 | 3 drops | 0 | r.t. | ~48% | 91% |
| 6 | 1 | 3% (S,S)-8 | 1 mL (xs) | 5 | r.t. | ~40% | 89% |
| 7 | 1 | 3% (S,S)-8 | 3 drops | 5 | 40° C. | ~83% | 97% |
| 8 | 1 | 3% (S,S)-8 | 3 drops | 0 | 40° C. | ~85% | 97% |
| 9[a] | 1 | 3% (S,S)-8 | 120 μL | 0 | 40° C. | ~85% | 97% |
| 10[b] | 1 | 3% (S,S)-8 | 1 mL (xs) | 5 | r.t. | ~50% | 89% |
| 11[b] | 1 | 3% (S,S)-8 | 3 drops | 5 | 40° C. | ~83% | 96% |
| 12[b,c] | 1 | 3% (S,S)-8 | excess | 5 | r.t. | 70–80% | 90% |

[a]Preparative scale (1.0 mmol); 1.2 eq $NaHCO_3$; reaction time 4 hrs; isolated yield.
[b]Reaction used 1.0 eq $Na_2CO_3$ in place of $NaHCO_3$.
[c]Substrate was butadiene monoepoxide (R = H).

GC evidence suggests that the initial product isolated from the reaction with $NaHCO_3$ is actually a carbonate, which loses $CO_2$ in the presence of acid (i.e. silica gel) to give the diol 15. It would appear that intramolecular hydrogen-bonding in the carbonate decreases the nucleophilicity of the primary alcohol and effectively blocks formation of any polymeric material. For highly water soluble products, dissolution of the product in the water phase is also expected to prevent polyalkylation (i.e. formation of dimer 16). In any case, this reaction represents an extremely useful procedure for the preparation of the enantiopure diol 15 from the racemic epoxide 1.

These results are significant in that they provide direct routes to enantiomerically enriched vinyl glycidol, a valuable chiral building block, in good yield and high e.e. Currently, the optically active diol is generally prepared by kinetic resolution of terminal epoxides (Jacobsen, 1997a), which gives maximum theoretical yield for either enantiomer of 50%.

E. Reactions of Carbonates and $CO_2$ in the Absence of Boron Reagent

The addition of $NaHCO_3$ to a vinyl epoxide, described above as a convenient one-step route to optically active 1,2-diols, was also examined in the absence of the boron cocatalyst, with somewhat surprising results: the cyclic carbonate 18 was isolated in good yield. The effects on this reaction of variation amount of $H_2O$, amount of $Bu_4NCl$, and catalyst loading are shown in Table IX. All reactions were conducted on a 0.25 mmol scale in $CH_2Cl_2$ at 0.1 M using 1.0 equiv. $NaHCO_3$ (see Example 12A). Unless otherwise noted, reactions were allowed to run for 18 h; in most cases, reactions required at least 8 h to go to completion.

TABLE IX

Addition of $NaHCO_3$ to Vinyl Epoxides in the Absence of Boron

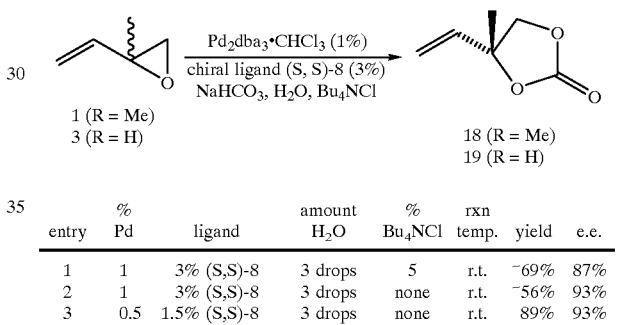

1 (R = Me)
3 (R = H)

18 (R = Me)
19 (R = H)

| entry | % Pd | ligand | amount $H_2O$ | % $Bu_4NCl$ | rxn temp. | yield | e.e. |
|---|---|---|---|---|---|---|---|
| 1 | 1 | 3% (S,S)-8 | 3 drops | 5 | r.t. | ~69% | 87% |
| 2 | 1 | 3% (S,S)-8 | 3 drops | none | r.t. | ~56% | 93% |
| 3 | 0.5 | 1.5% (S,S)-8 | 3 drops | none | r.t. | 89% | 93% |
| 4[a] | 1 | 3% (S,S)-8 | 3 drops | none | r.t. | 75% | 94% |

[a]Substrate was butadiene monoepoxide (R = H).

In the presence of 5% $Bu_4NCl$, formation of 18 proceeded at room temperature in good yield and e.e. (entry 1). When this reaction was repeated without the phase-transfer catalyst, the yield decreased, but the enantioselectivity improved (entry 2).

Catalyst loading was shown to be an important factor in obtaining 18 in high yield and e.e. When the reaction was carried out using 0.5% Pd and 1.5% ligand (entry 3), the product was obtained in 89% yield at 93% e.e.; after 26 hours, the yield had increased to 98% with no appreciable decrease in e.e. (92%).

The reaction in entry 2 was repeated using butadiene monoepoxide as the substrate, giving 75% isolated yield of 19 having and 94% e.e. (entry 6).

Carbonates and $CO_2$ can also be used as nucleophilic oxygen species in this reaction. The latter reaction gave a 75% yield of the cyclic carbonate in 88% e.e. using the standard 1% /3% catalyst levels (see Examples 12B–C). As for bicarbonate, optimal conditions were found to include lower catalyst loadings, and proper agitation of the reaction mixture was important. Good results were obtained using 0.5% Pd, 1.5% chiral ligand (S,S)-8, and 1.0 mL water at room temperature in $CH_2Cl_2$. The reaction was carried out under a $CO_2$ atmosphere, in a wide mouth vessel with moderate (1000 rpm) (to increase contact between phases), and gave a 98% yield and 90% e.e. after 8 hours. A phase transfer catalyst was not required.

III. Addition of Nitrogen Nucleophiles

Boron cocatalysis has also proven useful in Pd-catalyzed addition of nitrogen nucleophilic species, with alkyl or aralkyl amines being preferred species. For example, the addition of 2-aminoethanol to isoprene monoepoxide (Example 15), using 1% Pd complex, 3% racemic 8, and 1% boron cocatalyst (triisopropyl borate or $Et_3B$) in $CH_2Cl_2$ at room temperature, proceeded in high to quantitative yield with complete regioselectivity. It is also noteworthy that little or no polyalkylation, which can be common in reactions of primary amines, was observed. In the absence of the boron cocatalyst, the reaction was very sluggish. It is interesting to contrast this reaction with the similar reaction of N-Boc-protected ethanolamine (Example 16), which gave an 80% yield of the O-addition product.

IV. Utility

This section describes in more detail a few specific uses for products of the present reaction.

A. Routes to Optically Active 1,2-Diols

A number of alcohols that may be added to vinyl epoxides in accordance with the invention are, in effect, hydroxyl precursors, thus providing routes to enantiomerically enriched 1,2-diols. For example, with reference to Table VII above, the allyl ether 14 (entry 2) may be deprotected to the diol via Pd catalysis, while fluoride ion will remove the 2-TMS-ethyl protecting group from the product of entries 3–4 to give the diol. Similarly, when the products of entries 5–7 (keto and cyano vinyl ethers) are subjected to basic conditions, a retro-Michael reaction should occur to produce the diol. Finally, the benzyl and p-methoxybenzyl groups in entries 10 and 11 may be deprotected via transfer hydrogenolysis and DDQ oxidation, respectively. The latter reaction was carried out to give the acetal as a ~1.1:1 mixture of diastereomers. The acetal is a protected form of the diol, and may be readily cleaved under acidic conditions.

(14)

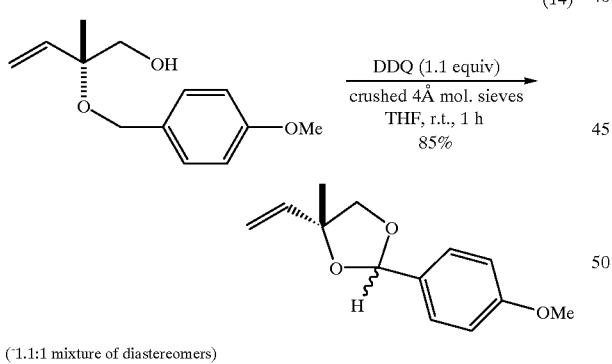

(~1.1:1 mixture of diastereomers)

As described above in Section E2, reagents such as carbonates and bicarbonates can be added, in the presence of water and, optionally, a phase transfer catalyst, to generate the 1,2-diols directly.

B. Differentially Protected Diols

The products of the alcohol addition reaction are also useful in that they directly provide selectively protected 1,2-diol precursors. It is particularly noteworthy that the protected alcohol is at the more hindered position, which is the position more difficult to selectively protect by more conventional strategies starting with a 1,2-diol.

C. Routes to Enantiomerically Enriched Oxygen Heterocycles

Certain alcohols were observed to give cyclic products in this reaction. For example, methyl glycolate produced the lactone 23 (eq 12). Presumably, the initially formed adduct rapidly closes onto the methyl ester to give the lactone.

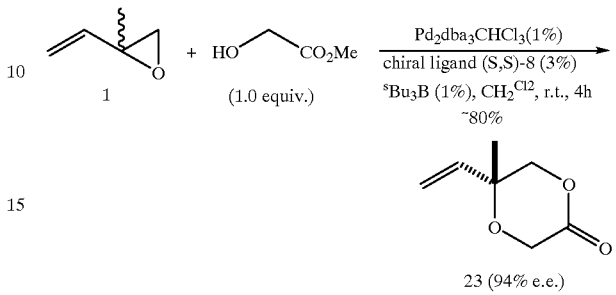

23 (94% e.e.)

The addition of acetol to isoprene monoepoxide 1, in the presence of 5% DMAP, gave the hemiketal 24 as a ~2.5:1 mixture of diastereomers (eq 13). When heated with $KHSO_4$ in THF, the product of this reaction eliminates water to give the diene 25, which is a good substrate for a Claisen rearrangement.

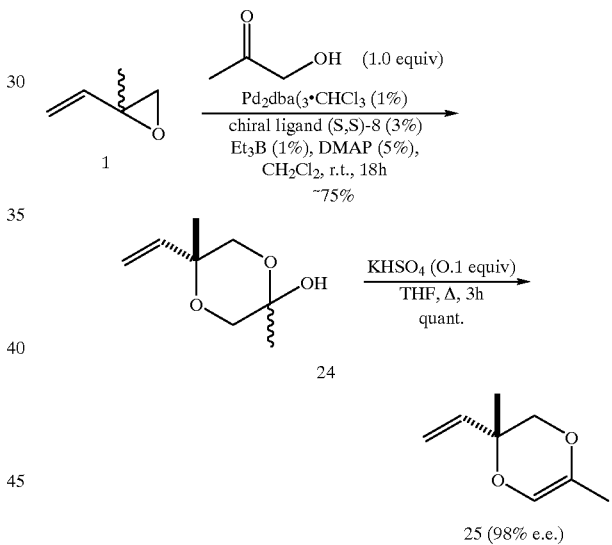

(~2.5:1 mixture of diastereomers)

Figure 4:
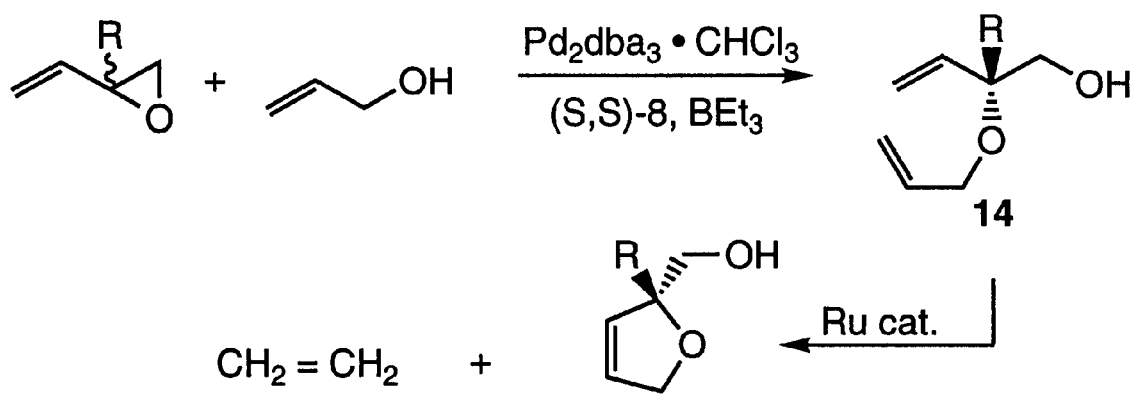
FIG. 4 shows a method for the preparation of enantiomerically enriched ribose and deoxyribose precursors, useful for the preparation of optically active nucleoside analogs.

The addition of an allyl alcohol (see, for example, Entry 2 of Table VI), provides a valuable route to precursors of nucleosides or nucleoside analogs having high enantiomeric purity. As shown in FIG. 4, vinyl allyl ether 14 (R=Me, 95% e.e.) ring-closing metathesis of the allyl alcohol adducts proceeded smoothly at room temperature in the presence of 2% $Cl_2(PCy_3)_2Ru=CHPh$ to provide the product dihydrofurans in 84% and 83% yield, respectively. The olefin metathesis reaction is well known and may also be catalyzed by tungsten, molybdenum, and rhenium complexes. No loss of stereochemical integrity was observed in the cyclization reactions; the optical purities of the products were identical to those of the starting materials. The product is a 2,5-dihydrofuran having one or two substituents at the 2 position (in furan numbering; position 4 in ribose numbering). The double bond may then be selectively oxidized or hydrated to give a ribose or deoxyribose structure.

Additional substrates for ring-closing metathesis reactions were also synthesized in accordance with the invention. Thus, treatment of isoprene monoepoxide or butadiene monoepoxide with 2.0 equiv. of allyl alcohol, 1-butenol, or 1-pentenol in the presence of 1% $Pd_2dba_3 \cdot CHCl_3$, 3% chiral ligand (S,S)-8, 1% $Et_3B$, and, for the last two cases, 5% DMAP, afforded the corresponding 1,2-adducts (e.g. 26, 27) in high yields (80–86%) and excellent enantioselectivity (90–96% e.e.) (see Examples 13A–B). Ring closing was carried out as above to give six-membered (e.g. 28, 29) and seven-membered rings. For formation of these larger rings, a larger amount of Ru catalyst (5 mol %) was used, as well as 30% $Ti(Oi\text{-}Pr)_4$ as a competitive Lewis acid to coordinate the OH function. Elevated temperature and extended reaction times were also required. For preparation of the oxepine (7-ring) system, the OH function was protected as the acetate Under these conditions, moderate-to-good yields were obtained of the cyclized compounds, again without loss of stereochemical integrity. (See Example 14).

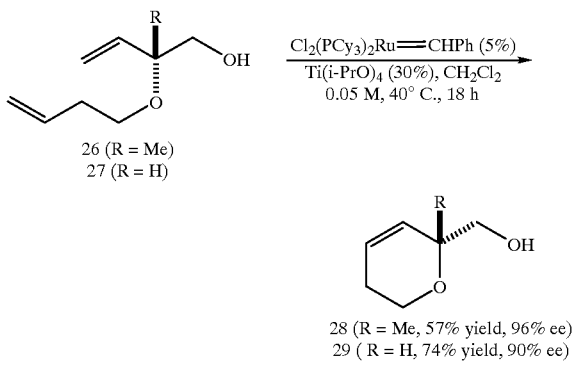

The results described herein show that the methods of the present invention provide rapid and convenient routes to a variety of useful optically active compounds; in particular, optically active 1,2diols and compounds derived from them. The selectivity and versatility of the reaction make the method ideal for the synthesis of pharmaceutical compounds, or compounds employed as intermediates in the synthesis of pharmaceutical compounds. The method is also applicable to preparing other biologically active compounds where high enantiomeric purity is important to activity.

EXAMPLES

The following examples illustrate but are not intended in any way to limit the invention.

Materials and Methods

All reactions were performed in oven-dried glassware, under an atmosphere of dry argon. Solvents were dried and distilled using standard procedures. Dichloromethane, acetonitrile, and triethylamine were distilled from calcium hydride, tetrahydrofuran was distilled from sodium/benzophenone, and toluene was distilled from sodium metal. Tris(dibenzylideneacetone) dipalladium(chloroform) ($Pd_2dba3 \cdot CHCl_3$) was prepared according to the method described by Ukai et al. Unless otherwise stated, all reactions were carried out at room temperature.

Compounds were characterized by NMR spectroscopy, IR spectroscopy, and elemental analysis. NMR spectra were recorded in $CDC_{13}$ or deuterobenzene using a Varian Gemini 300 spectrometer. IR spectra were recorded on liquid films (NaCl plates) employing a Perkin-Elmer Paragon 500 FTIR spectrophotometer. Elemental analyses were obtained from M—H—W Laboratories, Phoenix, Ariz.

Optical rotations were measured in a Jasco DIP-360 digital polarimeter in 5 cm cells at 25° C.

Chiral HPLC was performed on a Thermo Separation Products Spectra Series P100 HPLC using Chiralpak AD, AS and OD columns with detection at 254 nm. Chiral gas-liquid chromatography was performed on a HP 5890 capillary GC using a 30 m×0.252 mm J&W Cyclosil B column, with a split ratio of ~80:1 and 1.0 mL/min He as the carrier gas.

Example 1

Trialkylboron and Pd(0)-Catalyzed Addition of Alcohols to Vinyl Epoxides: General Procedure To an oven-dried test tube was added $Pd_2dba_3CHCl_3$ (0.01 equiv), chiral ligand (0.03 equiv), the alcohol R' OH (1.0 equiv), and a stirbar. The test tube was then placed under reduced pressure (vacuum pump) for 10 seconds and refilled with Ar; this purging procedure was repeated five times to ensure no oxygen remained in the reaction vessel. After being placed under an Ar atmosphere, freshly distilled and degassed $CH_2Cl_2$ was added (1.0 mL per mmol alcohol) and the resulting dark purple mixture was stirred at room temperature until it turned a deep orange color (roughly 15 min). During this time, a 1.0 M solution of trialkylborane in either THF or diethyl ether was added (0.01 equiv). To the solution of catalyst and alcohol was added neat isoprene monoepoxide 1 (1.0 equiv) and the solution immediately turned pale yellow. Stirring was continued for 3–18 h; when the reaction was complete, a deep orange or dark yellow color sometimes (although not invariably) appeared. The solvent was removed in vacuo, and the crude product was purified by flash chromatography on silica gel. Any remaining traces of solvent or moisture were removed under reduced pressure (vacuum pump).

For reactions carried out at elevated temperatures, a sealed tube was employed. In these cases the general procedure was the same, save that just prior to the addition of the vinyl epoxide the reaction vessel was heated to the desired temperature; the epoxide was then added and the tube was sealed and heated for the requisite time.

Example 2

Preparation of 2-(R)-2-Methoxybut-3-en-1-ol (4)

Following the general procedure of Example 1, butadiene monoepoxide (3) and methanol were converted into alcohol 4 with the following quantities of reagents and solvents: $Pd_2dba_3 \cdot CHCl_3$ (10 mg, 10 μmol), (S,S)-9 (24 mg, 30 μmol), a 1.0 M solution of $sBu_3B$ in diethyl ether (10 μL, 10 μmol), methanol (40 μL, 1.0 mmol), butadiene monoepoxide (80 μL, 1.0 mmol), $CH_2Cl_2$ (10 mL). The reaction time in this case was 3 h Flash chromatography of the crude material (silica gel, 4:1 pentane-ether) afforded 84 mg (82%) of 4 as a colorless oil in 89% e.e.(separated by chiral GLC, isothermal 50° C., (R)-(+)-isomer$_{rt}$=21.11 min, (S)(−)-isomer$_{rt}$= 23.38 min). [α]D=−41.4° (c 1.05, $CHCl_3$).

Example 3

Preparation of 2-(R)-2-(Prop2-en-1-oxy)but-3en-1-ol (7)

Following the general procedure of Example 1, butadiene monoepoxide (3) and allyl alcohol were converted into alcohol 7 with the following quantities of reagents and solvents: $Pd_2dba_3 \cdot CHCl_3$ (5.2 mg, 5 μmol), (S,S)-9 (11.8 mg, 15 μmol), a 1.0 M solution of ˢBu₃B in diethyl ether (5.0 μmol, 5 μmol), allyl alcohol (34 μL, 0.5 mmol), butadiene monoepoxide (40 μL, 0.5 mmol), CH₂Cl₂ (5.0 mL). The reaction time in this case was 18 h. Flash chromatography of the crude material (silica gel, 4:1 pentane-ether) afforded 52 mg (81%) of 7 as a colorless oil in 92% e.e.(separated by chiral GLC, isothermal 80° C., (S)-(−)-isomer$_{rt}$=16.23 min, (R)-(+)isomer$_{rt}$=17.03 min). [α]D=−34.2° (c 2.01, CHCl₃).

Example 4

Preparation of 2-(R)2-((4-Methoxyphenpl)methoxy)but-3-en-1-ol (12)

Following the general procedure of Example 1, butadiene monoepoxide (3) and p-methoxybenzyl alcohol were converted into alcohol 12 with the following quantities of reagents and solvents: Pd₂dba₃.CHCl₃ (5.2 mg, 5 μmol), (S,S)-9 (11.8 mg, 15 μmol), a 1.0 M solution of sBu₃B in diethyl ether (5.0 μL, 5 μmol), p-methoxybenzyl alcohol (62 μL, 0.5 mmol), butadiene monoepoxide (40 μL, 0.5 mmol), CH₂Cl₁₂ (5.0 μL). The reaction time in this case was 3 h. Flash chromatography of the crude material (silica gel, 4:1 pentane-ether) afforded 104.1 mg of 12 as a colorless oil in 84% e.e.(separated by chiral HPLC, Chiralpak OD column, eluted with 98:2 heptane-isopropanol @ 1.0 mL/min, (R)-(+)-isomer$_{rt}$=17.60 min, (S)-(−)-isomer$_{rt}$=22.88 min). [α]D=44.5 (c 1.14, CHCl₃).

Example 5

Preparation of 2-(R)2-Methoxy-2-methylbut-3-en-1-ol (6)

Following the general procedure of Example 1, isoprene monoepoxide (1) and methanol were converted into alcohol 6 with the following quantities of reagents and solvents: Pd₂dba₃ CHCl₃ (21 mg, 20 μmol), (S,S)-8 (41 mg, 60 μmol), a 1.0 M solution of Et₃B in THF (20 μL, 20 μmol), methanol (81 μL, 2.0 μmol), isoprene monoepoxide (196 μL, 2.0 mmol), CH₂Cl₂ (20 mL). The reaction time in this case was 3 h. Flash chromatography of the crude material (silica gel, 4:1 pentane-ether) afforded 205 mg (88%) of 6 as a colorless oil in 94% e.e.(separated by chiral GLC, isothermal 55° C., (S)-(+)-isomer$_{rt}$=38.43 min, (R)-(−)-isomer$_{rt}$=39.06 min). [α]D =−21.5° (c 1.01, CHCl₃).

Example 6

Preparation of 2-(R)2-Methyl2-(prop2-en-1-oxy)but-3-en-1-ol (14

Following the general procedure of Example 1, isoprene monoepoxide (1) and allyl alcohol were converted into alcohol 14 with the following quantities of reagents and solvents: Pd₂dba₃.CHCl₃ (5.2 mg, 5 μmol), (S,S)-8 (11.8 mg, 15 μmol), a 1.0 M solution of Et₃B in THF (5.0 μL, 5 μmol), allyl alcohol (34 μL, 0.5 mmol), isoprene monoepoxide (49 μL, 0.5 mmol), CH₂Cl₂ (5.0 mL). The reaction time in this case was 3 h. Flash chromatography of the crude material (silica gel, 4:1 pentane-ether) afforded approx. 71 mg of 14 as a colorless oil in 95% e.e.(separated by chiral GLC, isothermal 90° C., (R)(+)-isomer$_{rt}$=14.64 min, (S)-(−)-isomer$_{rt}$=15.58 min). [α]D=−7.9° (c 1.40, CHCl₃).

Example 7

Preparation of 2-(R)-2-(3-(RS)-3-Hydroxybut-1-oxy)-2-methylbut-3-en-1-ol

Following the general procedure of Example 1, isoprene monoepoxide (1) and 1,3-butanediol were converted into the title compound (see Table VII, entry 9) with the following quantities of reagents and solvents: Pd₂dba₃CHCl₃ (5.2 mg, 5 μmol), (S,S)-8 (11.8 mg, 15 μmol), a 1.0 M solution of ˢBu₃B in diethyl ether (5.0 μL, 5 μmol), 1,3-butanediol (45 μL, 0.5 mmol), isoprene monoepoxide (49 μL, 0.5 mmol), CH₂Cl₂ (5.0 mL). The reaction time in this case was 5 h. Flash chromatography of the crude material (silica gel, 4:1 pentane-ether) afforded 87.1 mg of the product as a colorless oil with an enantiomeric excess of 98% at the 2-stereocenter (separated by chiral GLC, isothermal 80° C, 2-(S)-(−)-diastereomerrt =22.47 min, 2-(R)-(+)-diastereomerrt =24.21 min). $^{13}$C NMR analysis indicated that the product was a 1:1 mixture of diastereomers, although both diastereomers appear to have identical $^{1}$H NMR spectra in both CDCl$_{13}$ and C₆D₆.

Example 8

Preparation of 2-(RS)-5-(R)-2,5-Dimethyl-5-vinyl-1,4-dioxacyclohexan-2-ol (24)

Following the general procedure of Example 1, isoprene monoepoxide (1) and acetol were converted into alcohol 24 with the following quantities of reagents and solvents: Pd₂dba₃.CHCl₃ (5.2 mg, 5 μmol), (S,S)-8 (11.8 mg, 15 μmol), a 1.0 M solution of Et₃B in THF (5.0 μL, acetol (34 μL, 0.5 mmol), isoprene monoepoxide (49 μL, 0.5 mmol), CHCl (5.0 mL). In this case, DMAP (3 mg, 25 μmol) was also added to the reaction mixture at the same stage as the addition of Pd₂dba₃.CHCl₃, (S,S)-8, and acetol; the reaction time was 18 h. Flash chromatography of the crude material (silica gel, 4:1 pentane-ether) afforded 79.1 mg of 24 as a colorless oil. $^{1}$H NMR analysis indicated that the product was a ~2.5:1 mixture of diastereomers.

Example 9

Preparation of 2-(S)2-Methoxy-2-phenyl-but-3-en-1-ol

To an oven-dried test tube was added Pd₂dba₃.CHCl₃ (5.2 mg, 5 μmol), chiral ligand (S,S)8 (10.4 mg, 15 μmol), DMAP (3 mg, 25 μmol) and a stirbar. Three drops dry THF were added to wet the catalyst, and the tube was then placed under reduced pressure (vacuum pump) for 10 sec and refilled with Ar; this purging procedure was repeated five times to ensure no oxygen remained in the reaction vessel. After being placed under an Ar atmosphere, freshly distilled and degassed THF was added (5 mL) and the resulting dark purple mixture was stirred at room temperature until it turned a deep orange color (roughly 5 min). During this time, neat 2-methoxy4,4,5,5-tetramethyl-[1,3,2]dioxaborolane (79 mg, 0.50 mmol) was added. Finally, 2-phenyl-vinyloxirane (75 μL, 0.50 mmol) was added to the mixture of catalyst and borolane and the solution turned bright yellow. Stirring was continued for 18 h, at which point the solvent was removed in vacuo. The crude product was purified by flash chromatography on silica gel (pentane-diethyl ether, 4:1), to give ~125 mg (~70%) of the addition product as a colorless oil in 91% ee (separated by chiral GLC, Cyclodex column, isothermal 120° C., (S)isomer$_{rt}$= 33.98 min, (R)-isomer$_{rt}$=34.86 min.) $^{1}$H NMR (300 MHz) δ 1.89 (Br s, 1H), 3.19 (s, 3H), 3.81 (d, 1H, J=11 Hz), 3.85 (d, 1H, J=11 Hz, 5.39 (d, 1H, J=18 Hz), 5.47 (d, 1H, J=11 Hz), 6.07 (dd, 1H, J=11,18 Hz), 7.26–7.40 (m, 5H); $^{13}$C NMR (75.5 MHz) δ 51.3, 67.3, 82.2, 118.3, 127.0, 127.6, 128.4, 136.9, 139.8. Anal. Calc'd. for C₁₁H₁₄O₂: C, 74.13; H, 7.92. Found: C, 74.04; H, 7.78.

Example 10

Preparation of 2-(S)-2-Benzyloxy-2-phenyl-but-3-en-1-ol

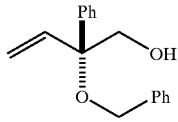

To an oven-dried test tube was added Pd$_2$dba$_3$CHCl$_3$ (2.6 mg, 2.5 μmol), chiral ligand (S,S)-8 (5.2 mg, 7.5 μmol), DMAP (1.5 mg, 12 μmol) and a stirbar. Three drops dry THF were added to wet the catalyst, and the tube was then placed under reduced pressure (vacuum pump) for 10 sec and refilled with Ar; this purging procedure was repeated five times to ensure no oxygen remained in the reaction vessel. After being placed under an Ar atmosphere, freshly distilled and degassed THF was added (2.5 mL) and the resulting dark purple mixture was stirred at room temperature until it turned a deep orange color (roughly 5 min). During this time, neat benzyl borate (83 mg, 0.25 mmol) was added. Finally, 2-phenyl-vinyloxirane (38 μL, 0.25 mmol) was added to the mixture of catalyst and borolane and the solution turned bright yellow. Stirring was continued for 18 h, at which point the solvent was removed in vacuo. The crude product was purified by flash chromatography on silica gel (pentane-diethyl ether, 4:1), to give ~38 mg (~60%) of the addition product as a colorless oil in 84% ee (separated by chiral GLC, Cyclosil B column, isothermal 180° C., (R)-isomer$_{rt}$=51.69 min, (S)-isomer$_{rt}$=52.70 min). $^1$H NMR (300 MHz) δ 1.99 (br s, 1H), 3.91 (d, 1H, J=11 Hz), 3.96 (d, 1H, J=11 Hz), 4.38 (d, 1H, J=11 Hz), 4.44(d, 1H j=11 Hz), 5.49 (d, 1H, J=18 Hz), 5.52 (d, 1H, J=10 Hz), 6.18 (dd, 1H, J=10, 18 Hz), 7.29–7.41 (m, 8H), 7.48 (d, 2H, J=7 Hz); $^{13}$C NMR (75.5 MHz) δ 65.2, 67.6, 82.4, 118.3 127.0, 127.3, 127.4, 127.7, 128.37, 128.40, 137.3, 138.7, 140.0. Anal. Calc'd. for C$_{17}$H$_{18}$O$_2$: C, 80.28; H, 7.13. Found: C, 80.14; H, 7.08.

Example 11

Preparation of Enantiomerically Enriched Diols

Example 11A.

Preparation of 2-(R)-2-Methylbut-3-en-1.2-diol (15) by Addition of NaHCO$_3$ to Isoprene Monoepoxide

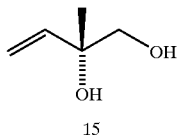

15

To an oven-dried sealed tube was added (dba)$_3$Pd$_2$·CHCl$_3$ (10.4 mg, 10 μmol), chiral ligand (S,S)-8 (20.8 mg, 30 μmol), NaHCO$_3$ (101 mg, 1.2 mmol), deionized water (120 μL), and a stirbar. The flask was then placed under reduced pressure (vacuum pump) for 10 sec and refilled with Ar; this purging procedure was repeated five times to ensure no oxygen remained in the reaction vessel. After being placed under an Ar atmosphere, freshly distilled methylene chloride was added (10 mL) and the resulting dark purple mixture was stirred at room temperature until it turned a deep orange color (roughly 5 min). During this time, a 1.0 M solution of triethylborane in THF was added (10 μL, 10 μmol). The flask was then heated to 40° C. and neat isoprene monoepoxide (100 μL, 1.0 mmol) was added to the suspension of catalyst and NaHCO$_3$; the solution immediately turned pale yellow. The reaction vessel was sealed and stirring was continued for 4 h, at which point the original deep orange color reappeared. The solution was dried (MgSO$_4$), then the solvent was removed in vacuo and the crude product was purified by flash chromatography on silica gel (1:1 pentane-diethyl ether). Any remaining traces of solvent or moisture were removed under reduced pressure (vacuum pump), to give 93 mg (91%) of the diol as a colorless oil in 97% ee (separated by chiral GLC, Cyclosil B column, isothermal 90° C., (S)-(−)-isomer$_{rt}$=14.03 min, (R)-(+)-isomer$_{rt=14.61}$ min). [α]D=+4.78° (c=2.50, CHCl$_3$); $^1$H NMR (300 MHz): δ 1.26 (s, 3H), 2.03 (br s, 2H), 3.43 (d, 1H, J=11 Hz), 3.50 (d, 1H, J=11 Hz), 5.18 (d, 1H, j=11 Hz), 5.33 (dd, 1H, J=1,17 Hz), 5.87 (dd, 1H, J=11, 17 Hz).

Example 11B.

Preparation of 2-(R)-But-3-en-1.2-diol (17) by Addition of Na$_2$CO$_3$ to Butadiene Monoepoxide

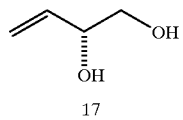

17

To a 20 mm ×150 mm test tube was added (dba)$_3$Pd$_2$·CHCl$_3$ (13 mg, 13 μmol), chiral ligand (S,S)-9 (30 mg, 38 μmol), Bu$_4$NCl·H$_2$O (18 mg, 63 μmol), Na$_2$CO$_3$ (159 mg, 1.5 mmol) and 2×10 mm stirbar. The flask was then placed under reduced pressure (vacuum pump) for 10 sec and refilled with Ar; this purging procedure was repeated five times to ensure no oxygen remained in the reaction vessel. After being placed under an Ar atmosphere, freshly distilled methylene chloride was added (12.5 mL) and the resulting dark purple mixture was stirred at room temperature until it turned a deep orange color (roughly 5 min). During this time, a 1.0 M solution of triethylborane in THF was added (6.25 μL, 6.25 μmol). At this point, neat butadiene monoepoxide (101 μL, 1.25 mmol) was added and the solution immediately turned pale yellow; finally, deionized water (5 mL) was added. The reaction was stirred vigorously for 3 h, at which point the dark orange color reappeared. The phases were separated, and the CH$_2$Cl$_2$ layer was extracted once with water (1.0 mL), then the CH$_2$Cl$_2$ was discarded. The aqueous fractions were combined and acidified with saturated NaHSO$_4$, and then saturated with solid NaCl. Next, the aqueous phase was extracted with EtOAc (7∞5 mL), then the organic fractions were combined, dried (MgSO$_4$), and the solvent was removed in vacuo. The crude product was purified by flash chromatography through a plug of silica gel (diethyl ether then EtOAc) to give 81 mg (74%) of the diol as a colorless oil in 92% ee (separated by chiral GLC, Cyclosil B column, initial value: 100° C., initial time: 0 min, rate: 2° C./min, final value: 60° C., final time: 30 min, (s)-(−)-isomer$_{rt}$=14.56 min, (R)-(+)-isomer$_{rt}$=15.27 min). [α]D=+5.1° (c 2.15, CHCl$_3$); [α]D=+35.3° (c 1.80, i-PrOH); IR: 3374, 1646, 1427, 1139, 1074, 1030, 929, 867 cm$^{-1}$ $^1$H NMR (300 MHz): δ 2.07 (br s, 2H), 3.50 (dd, 1H, J=7, 11 Hz), 3.67 (dd, 1H, J=3, 11 Hz), 4.22–4.27 (m, H), 5.22 (d, 1H, J=10 Hz), 5.35 (d, 1H, J=17 Hz), 5.84 (ddd, 1H, J=6, 10, 17 Hz).

Example 11C.

Preparation of 2-(R)-2-Methylbut-3-en-1,2-diol (15) by Addition of $H_2O$ to Isoprene Monoepoxide To a 25 mL round-bottom flask was added (dba)$_3$Pd$_2$.CHCl$_3$ (10.4 mg, 10 µmol), chiral ligand (S,S)-8 (20.8 mg, 30 µmol), Bu$_4$NCl.H$_2$O (14 mg, 50 µmol), and a stirbar. The flask was then placed under reduced pressure (vacuum pump) for 10 sec and refilled with Ar; this purging procedure was repeated five times to ensure no oxygen remained in the reaction vessel. After being placed under an Ar atmosphere, freshly distilled methylene chloride was added (10 mL) and the resulting dark purple mixture was stirred at room temperature until it turned a deep orange color (roughly 5 min). During this time, a 1.0 M solution of triethylborane in THF was added (10 µL, 10 µmol). At this point, neat isoprene monoepoxide (100 µL, 1.0 mmol) was added and the solution immediately turned pale yellow; finally, deionized water (4 mL) was added. The reaction was stirred vigorously for 4 h, at which point the dark orange color reappeared. The aqueous phase was diluted with brine (5 mL) and extracted with EtOAc (5 ∞3 mL), then the organic fraction were combined, dried (MgSO$_4$), and the solvent was removed in vacuo. The crude product was purified by flash chromatography on silica gel (1:1 pentane-diethyl ether) to give 89 mg (87%) of the diol as a colorless oil in 93% ee. [α]D=+4.45° (c=2.58, CHCl$_3$). Separation conditions and spectra were the same as those given above (Example 11A)

Example 12

Preparation of Enantiomerically Enriched Carbonates in the Absence of Boron

Example 12A. Preparation of 4-(R)4-Methyl4-vinyl-[1,3]dioxolan-2-one (18) by Treatment of Isoprene Monoepoxide with NaHCO$_3$

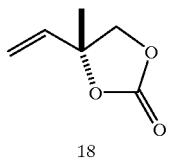

18

To a 25 mL round-bottom flask was added (dba)$_3$Pd$_2$.CHCl$_3$ (5.2 mg, 5.0 µmol), chiral ligand (S,S)-8 (10.4 mg, 15 µmol), NaHCO$_3$ (168 mg, 2.0 mmol), and a stirbar. The flask was then placed under reduced pressure (vacuum pump) for 10 sec and refilled with Ar; this purging procedure was repeated five times to ensure no oxygen remained in the reaction vessel. After being placed under an Ar atmosphere, freshly distilled methylene chloride was added (10 mL) and the resulting dark purple mixture was stirred at room temperature until it turned a deep orange color (roughly 5 min). At this point, neat isoprene monoepoxide (100 µL, 1.0 mmol) was added to the suspension of catalyst and NaHCO$_3$; the solution immediately turned pale yellow. Finally, deionized water (4 mL) was added, and the biphasic mixture was stirred for 26 h. At this time, the phases were separated and the aqueous layer was extracted with CH$_2$Cl$_2$ (3×5 mL). Next, the organic fractions were combined and washed once with brine, dried (MgSO$_4$), and the solvent removed in vacuo. The crude product was purified by flash chromatography on silica gel (4:1 pentane-diethyl ether) and any remaining traces of solvent or moisture were removed under reduced pressure (vacuum pump), to give 112 mg (88%) of the cyclic carbonate as a colorless oil in 93% ee. (separated by chiral GLC, Cyclosil B column, isothermal 120° C., (R)-(+)-isomer$_{rt}$=10.54 min, (S)-(−)-isomer$_{rt}$=11.34 min) exhibited [α]D=−17.3° (c 2.10, CHCl$_3$); $^1$H NMR (300 MHz): δ 1.58 (s, 3H), 4.16 (d, 1H, J=8 Hz), 4.25 (d, 1H, J=8Hz), 5.30 (d, 1H, J=11 Hz), 5.42 (d, 1H, J=17Hz), 5.92 (dd, 1H, J=11, 17Hz).

Example 12B.

Preparation of 4(R)4-Methyl-4-vinyl-[1,3]dioxolan-2-one (18) by Treatment of Isoprene Monoepoxide with $CO_2$ To a 16×100 mm test tube was added (dba)$_3$Pd$_2$.CHCl$_3$ (2.6 mg, 2.5 µmol), chiral ligand (S,S)-8 (5.2 mg, 7.5 µmol), and a 2×10 mm stirbar. The flask was then placed under reduced pressure (vacuum pump) for 10 sec and refilled with Ar; this purging procedure was repeated five times to ensure no oxygen remained in the reaction vessel. After being placed under an Ar atmosphere, freshly distilled methylene chloride was added (5 mL) and the resulting dark purple mixture was stirred at room temperature until it turned a deep orange color (roughly 5 min). At this point, neat isoprene monoepoxide (50 µL, 0.50 mmol) was added and the solution immediately turned pale yellow. Next, deionized water (1 mL) was added, and the biphasic mixture was placed under a CO$_2$ atmosphere (CO$_2$ balloon) and stirred at 1000 rpm for 8 h. At this time, the phases were separated and the aqueous layer was extracted with CH$_2$Cl$_2$ (3×5 mL). Next, the organic fractions were combined and washed once with brine, dried (MgSO$_4$), and the solvent removed in vacuo. The crude product was purified by flash chromatography on silica gel (4:1 pentane-diethyl ether) and any remaining traces of solvent or moisture were removed under reduced pressure (vacuum pump), to give 56 mg (87%) of the cyclic carbonate as a colorless oil in 90% ee. [α]D=−16.8° (c 3.46, CHCl$_3$). Separation conditions and spectra were the same as those given above.

Note: Extended reaction times result in partial racemization of the product; for example, after a reaction time of 12 h, the product was obtained in 88% ee. Also, the rate of stirring (i.e. the rate of mixing between the organic and aqueous phases) is important in determining the rate of reaction; for example, when the reaction was stirred at 500 rpm, it progressed to only 5% completion after 13 h. The size of reaction flask and/or stirbar can also affect the rate of mixing. Moreover, too-rapid mixing can result in lower enantioselectivity. For example, when the reaction was carried out using very vigorous stirring, all of the starting material was consumed after 5 h, but the product was obtained in 28% ee.

Example 12C.

Preparation of 4-(R4-Vinyl-[1,3]dioxolan-2-one (19)

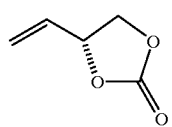

19

To an oven-dried 25 mL round-bottom flask was added (dba)$_3$Pd$_2$.CHCl$_3$ (5.8 mg, 7.5 µmol), chiral ligand (S,S)-9

(10.4 mg, 23 μmol), NaHCO$_3$ (252 mg, 3.0 mmol), and a 9×15 mm stirbar. The flask was then placed under reduced pressure (vacuum pump) for 10 sec and refilled with Ar; this purging procedure was repeated five times to ensure no oxygen remained in the reaction vessel. After being placed under an Ar atmosphere, freshly distilled methylene chloride was added (15 mL) and the resulting dark purple mixture was stirred at room temperature until it turned a deep orange color (roughly 5 min). At this point, neat butadiene monoepoxide (120 μL, 1.5 mmol) was added to the suspension of catalyst and NaHCO$_3$; the solution immediately turned pale yellow. Finally, deionized water (6 mL) was added, and the biphasic mixture was stirred at 500 rpm for 5 h. At this time, the phases were separated and the aqueous layer was extracted with CH$_2$Cl$_2$ (3×5 mL). Next, the organic fractions were combined and washed once with brine, dried (MgSO$_4$), and the solvent removed in vacuo. The crude product was purified by flash chromatography on silica gel (4:1 pentane-diethyl ether) and any remaining traces of solvent or moisture were removed under reduced pressure (vacuum pump), to give 151 mg (89%) of the cyclic carbonate as a colorless oil in 92% ee (separated by chiral GLC, Cyclosil B column, isothermal 120° C., (R)-(+)-isomer$_{rt}$=11.25 min, (S)-(-)-isomer$_{rt}$=11.78 min.). [α]D=+20.5° (c 2.80, CHCl$_3$); $^1$H NMR (300 MHz): δ 4.13 (dd, 1H, J=8, 8 Hz), 4.58 (dd, 1H, J=8, 8 Hz), 5.10 (ddd, 1H, J=7, 8, 8 Hz), 5.42 (d, 1H, J=11 Hz), 5.49 (d, 1H, J=17 Hz), 5.88 (ddd, 1H, J=7, 11, 17 H Hz).

Note: Again, the rate of stirring and size of stirbar (i.e. the rate of mixing between the organic and aqueous phases) is important in determining the rate and selectivity of this reaction. For example, when the reaction was carried out using slower (200 rpm) stirring, 18 h were required for completion and the yield was lower (76% yield, 92% ee). When the reaction was stirred too quickly, the enantioselectivity decreased somewhat; for example, stirring at 1000 rpm gave a reaction time of 3 h, but the product was obtained in 89% ee.

Examples 13–14

Preparation of Optically Active Dialkenyl Ethers and Cyclization to Optically Active Cyclic Ethers Example 13.

Addition of Alcohols CH$_2$=CH(CH$_2$)$_n$OH to Vinyl Epoxides

Example 13A.

Preparation of 2-(R)-2-But-3-enyloxybut-3-en-1-ol (27)

27

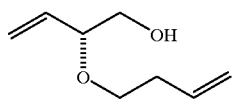

To an oven dried test tube was added Pd$_2$dba$_3$.CHCl$_3$ (5.2 mg, 5.0 μmol), chiral ligand (S,S)-9 (11.8 mg, 15 μmol), DMAP (6.2 mg, 50 μmol) and a stirbar. Several drops of CH$_2$Cl$_2$ were then added to wet the catalyst, and the test tube was immediately placed under reduced pressure (vacuum pump) for 10 sec and refilled with Ar. This purging procedure was repeated five times to ensure no oxygen remained in the reaction vessel. After being placed under an Ar atmosphere, freshly distilled and degassed methylene chloride was added (10 mL) and the resulting dark purple mixture was stirred at room temperature until it turned a deep orange color (roughly 15 min). During this time, the 3-butenol (172 μL, 2.0 μmol) and a 1.0 M solution of Et$_3$B in THF was added (5.0 μL, 5.0 μmol). To the solution of catalyst and alcohol was added neat butadiene monoepoxide (81 μL, 1.0 μmol) and the solution immediately turned pale yellow. Stirring was continued for 4 h. The solvent was removed in vacuo. Flash chromatography of the crude material (silica gel, 4:1 pentane-ether) afforded 116 mg (82%) of 27 as a colorless oil in 90% ee (separated by chiral GLC, Cyclosil B column, isothermal 100° C., (S)-(+)-isomer$_{rt=11.97}$ min, (R)-(-)-isomer$_{rt}$=12.20 min). [α]D=-50.0° (c 2.20, CHCl$_3$); $^1$H NMR (300 MHz): δ 2.09 (br s, 1H), 2.28–2.35 (m, 2H), 3.32–3.40 (m, 1H), 3.46–3.66 (m, 3H), 3.77–3.83 (m, 1H), 5.01 (d, 1H, J=11 Hz), 5.10 (d, 1H, J=17 Hz), 5.23 (d, 1H, J=10 Hz), 5.28 (d, 1H, J=17 Hz), 5.60–5.84 (m, 2H); $^{13}$C NMR (75 MHz): δ 34.2, 65.3, 67.9, 81.7, 116.6, 118.7, 135.2, 135.2. Anal. Calcd. for C$_8$H$_{14}$O$_2$: C, 67.57; H, 9.92; found C, 67.36; H, 9.80.

Example 13B.

Preparation of 2-(R)-2-Pent-4enyloxy-but-3-en-1-ol

Following the general procedure in Example 13A, 4-pentenol was added to butadiene monoepoxide, using the following quantities of reagents and solvents: Pd$_2$dba$_3$.CHCl$_3$ (5.2 mg, 5.0 μmol), (S,S)-9 (11.8 mg, 15 μmol), DMAP (6.2 mg, 50 μmol), a 1.0 M solution of Et$_3$B in THF (5.0 μL, 5.0 μmol), 4-pentenol (207 μL, 2.0 mmol), butadiene monoepoxide (81 μL, 1.0 mmol), CH$_2$Cl$_2$ (10 mL). The reaction time in this case was 4 h. Flash chromatography of the crude material (silica gel, 4:1 pentane-ether) afforded 131 mg (84%) of a colorless oil in 90% ee (separated by chiral GLC, Cyclosil B column, isothermal 120° C., (S)-(+)-isomer$_{rt}$=9.33 min, (R)-(-)-isomer$_{rt}$=9.68 min). [α]D=-33.2° (c 2.86, CHCl$_3$); $^1$H NMR (300 MHz) δ 1.66 (quint 2H, J=7 Hz), 2.07–2.26 (m, 3H), 3.28–3.61 (m, 4H), 3.75–3.81 (m, 1H), 4.94 (d, 1H, J=11 Hz), 5.00 (d, 1H, J=17 Hz), 5.24 (d, 1H, J=9 Hz), 5.28 (d, 1H, J=17 Hz), 5.60–5.83 (m, 2H). $^{13}$C NMR (75.5 MHz) δ 28.9, 30.4, 65.2, 68.2, 81.6, 114.8, 118.7, 135.4, 138.2. Anal. Calc'd. for C$_9$H$_{16}$O$_2$: C, 69.19; H, 10.32. Found: C, 69.23; H, 10.14.

Example 13C.

Preparation of 2-(R)-2-Hex-5-enyloxy-but-3-en-1-ol

Following the general procedure of Example 13A, 5-hexenol was added to butadiene monoepoxide, using the following quantities of reagents and solvents: Pd$_2$dba$_3$.CHCl$_3$ (5.2 mg, 5.0 μmol), (±)-8 (10.4 mg, 15 μmol), DMAP (6.2 mg, 50 μmol), a 1.0 M solution of Et$_3$B in THF (5.0 μL, 5.0 μmol), 5-hexenol (240 μL, 2.0 mmol), butadiene monoepoxide (81 μL, 1.0 μmol), CH$_2$Cl$_2$ (10 mL). The reaction time in this case was 4 h. Flash chromatography of the crude material (silica gel, 4:1 pentane-ether) afforded ~135 mg (80%) of a colorless oil. (enantiomers separated by chiral GLC, Cyclosil B column isothermal 120° C, (S)-(+)-isomer$_{rt}$=15.52 min, (R)-(-)-isomer$_{rt}$=16.21 min). $^1$H NMR (300 MHz) δ 1.36–1.43 (m, 2H), 1.50–1.58 (m, 2H), 1.97–2.04 (m, 2H), 2.50 (br s, 1H), 3.24–3.31 (m, 1H), 3.43–3.53 (m, 3H), 3.71–3.75 (m,1H), 4.89 (d, 1H, J=11 Hz), 4.94 (d, 1H, J=19Hz), 5.20 (d, 1H, J=9 Hz), 5.24 (d, 1H, J=17 Hz), 5.57–5.78 (m, 2H); $^{13}$C NMR (75.5 MHz) δ 25.3, 29.1, 33.4, 65.1, 68.6, 81.6, 114.5, 118.4, 135.4, 138.5. Anal. Calc'd. for C$_{10}$H$_{18}$O$_2$: C, 70.55; H, 10.66. Found: C, 70.66; H, 10.43.

Example 13D.

Preparation of 2-(R)-2-Methyl-2-But-3-enyloxy-2-methyl-but-3-en-1-ol (24)

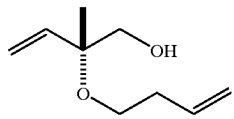

26

Following the general procedure of Example 13A, isoprene monoepoxide and 3-butenol were converted into alcohol 26 using the following quantities of reagents and solvents: Pd$_2$dba$_3$.CHCl$_3$ (10.4 mg, 10 μmol), (S,S)-8 (20.8 mg, 30 μmol), DMAP (6.2 mg, 50 μmol), a 1.0 M solution of Et$_3$B in THF (10 μL, 10 μmol), 3-butenol (172 μL, 2.0 mmol), isoprene monoepoxide (99 μL, 1.0 mmol), CH$_2$Cl$_2$ (10 mL). The reaction time in this case was 3 h, while the reaction temperature was 40° C. (For reactions carried out at elevated temperatures, a sealed tube was employed. In these cases the general procedure was the same, save that just prior to the addition of butadiene monoepoxide the reaction vessel was heated to the desired temperature; the epoxide was then added and the tube was sealed and heated for the requisite time.) Flash chromatography of the crude material (silica gel, 4:1 pentane-ether) afforded 260 mg (83%) of 26 as a colorless oil in 96% ee (separated by chiral GLC, Cyclosil B column, isothermal 80° C., (R)-(−)-isomer$_{rt}$=34.78 min, (S)-(+)-isomer$_{rt}$=36.66 min). [α]D=−10.6° (c 2.29, CHCl$_3$); $^1$H NMR (300 MHz): δ 1.26 (s, 3H), 2.01 (br s, 1H), 2.24–2.30 (m, 2H), 3.24–3.48 (m, 4H), 5.01 (d, 1H, J=11 Hz) 5.06 (d1H, J=18 Hz), 5.16–5.26 (m, 2H), 5.72–5.86 (m, 2H); $^{13}$C NMR (75 MHz): δ 18.4, 34.7, 61.7 69.2 77.6, 116.3, 116.5, 135.3, 139.9. Anal. Calcd. for C$_9$H$_{16}$O$_2$: C, 69.19; H, 10.32; found C, 69.30; H, 10.15.

Example 13E.

Preparation of 2-(R)-2-Methyl2-pent-4-enyloxn-but-3-en-1-ol

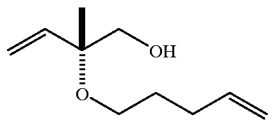

Following the general procedure of Example 13A, 4-pentenol was added to isoprene monoepoxide using the following quantities of reagents and solvents: Pd$_2$dba$_3$.CHCl$_3$ (10.4 mg, 10 μmol), (S,S)-8 (20.8 mg, 30 μmol), DMAP (6.2 mg, 50 μmol), a 1.0 M solution of Et$_3$B in THF (10 μL, 10 μmol), 4-pentenol (207 μL 2.0 mmol), isoprene monoepoxide (99 μL, 1.0 mmol), CH$_2$Cl$_2$ (10 mL). The reaction time in this case was 2 h, while the reaction temperature was 40° C. Flash chromatography of the crude material (silica gel, 4:1 pentane-ether) afforded 147 mg (86%) of a colorless oil in 91% ee (separated by chiral GLC, Cyclosil B column, isothermal 110° C., (R)-(−)-isomer$_{rt}$=18.84 min, (S)-(+)-isomer$_{rt}$=19.86 min). [α]D=−12.0° (c 2.54, CHCl$_3$); $^1$H NMR (300 MHz) δ 1.25 (s, 3H), 1.61 (quint, 2H, J=7 Hz), 2.06–2.13 (m, 3H), 3.28–3.33 (m, 2H), 3.38 (d, 1H, J=11 Hz), 3.45 (d, 1H, J=11 Hz), 4.94 (d, 1H, J=11 Hz), 4.99 (d, 1H, J=17 Hz), 5.20 (d, 1H, J=18 Hz), 5.23 (d, 1H, J=11 Hz), 5.74–5.83 (m, 2 H). $^{13}$C NMR (75.5 MHz): δ 18.4, 29.4, 30.4, 61.7, 69.4, 77.5, 114.6, 116.6, 138.4, 140.0. Anal. Calc'd. for C$_{10}$H$_{18}$O$_2$: C, 70.55; H, 10.66. Found: C, 70.43; H, 10.54.

Example 13F.

Preparation of Acetate-Protected Substrates: General Procedure

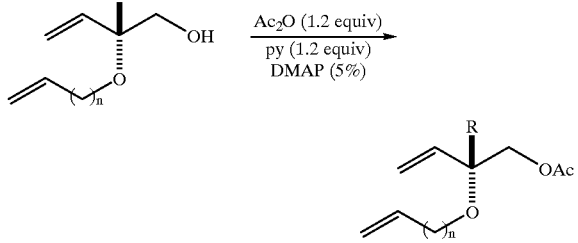

To a stirred solution of the alcohol in CH$_2$Cl$_2$ (1 mL per mmol alcohol) was added pyridine (1.2 equiv), DMAP (0.05 equiv), and acetic anhydride (1.2 equiv). Stirring was continued for 3–18 h, at which time the solvent was removed in vacuo, and the crude material was purified by flash chromatography on silica gel. Any remaining traces of solvent or moisture were removed under reduced pressure (vacuum pump).

Example 14

Ring-Closing Metathesis Reactions: General Procedure

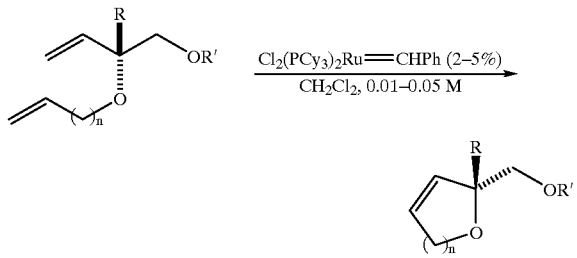

(Bis(tricyclohexylphosphine)benzylidene ruthenium (IV) dichloride (Grubbs catalyst) was purchased from Strem and used without further purification. To a stirred solution of allyl alkenyl ether in dry, degassed CH$_2$Cl$_2$ (20–100 mL per mmol substrate) was added a solution of Cl$_2$(PCy$_3$)$_2$Ru=CHPh (0.02—0.05 equiv) in CH$_2$Cl$_2$ (0.2 mL per mmol substrate). In some cases, neat Ti($^i$PrO)$_4$ (0.3 equiv) was also added at this time. The resulting purple solution was stirred at room temperature for 3–24 h, during which time the colour changed to light orange (after ~30 min), then to dark green/brown (after ~18 h). When the reaction was complete, the solvent was removed in vacuo, and the crude material was purified by flash chromatography on silica gel. Any remaining traces of solvent or moisture were removed under reduced pressure (vacuum pump).

For reactions carried out at elevated temperatures, a sealed tube was employed. In these cases the general procedure was the same, save that just prior to the addition of the ruthenium catalyst, the reaction vessel was heated to the desired temperature; the catalyst solution was then added and the tube was sealed and heated for the requisite time.

Example 14A.

Preparation of (2-(R)-2-Methyl-2,5-dihydro-furan-2-yl)methanol

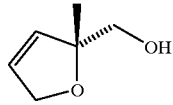

Following the general procedure above, the allyl ether 14 was converted into the cyclic ether using the following quantities of reagents and solvents: compound 14 (150 mg, 1.05 mmol), Cl$_2$(PCy$_3$)$_2$Ru=CHPh (17 mg, 0.02 mmol), CH$_2$Cl$_2$ (21 mL). The reaction time in this h. Flash chromatography of the crude material (silica gel, 2:1 pentane-ether) afforded 101 mg (84%) of a colorless oil in 95% ee (separated by chiral GLC, Cyclosil B column, isothermal 80° C., (R)-(+)-isomer$_{rt}$=20.98 min, (S)-(−)-isomer$_{rt}$=22.00 min). [α]D=+25.3° (c 0.60, CHCl$_3$); $^1$H NMR (300 MHz) δ 1.22 (s, 3H), 2.12 (br s, 1H), 3.46–3.54 (m, 2H), 4.64 (br s, 2H), 5.65 (dt, 1H, J=6, 2 Hz), 5.91 (br d, 1H, J=6 Hz); $^{13}$C NMR (75.5 MHz): δ 22.3, 68.3, 75.1, 90.7, 127.4, 131.1. Anal. Calc'd. for C$_6$H$_{10}$O$_2$: C, 63.14; H, 8.83. Found: C, 62.95; H, 8.65.

Example 14B.

Preparation of (2-(R)-5,6Dihydro-2H-pyran-2-yl)-methanol (29)

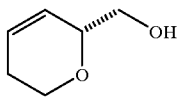

Following the general procedure above, the allyl ether 27 was converted into the cyclic ether 29 using the following quantities of reagents and solvents: compound 27 (100 mg, 0.70 mmol), Cl$_2$(PCy$_3$)$_2$Ru=CHPh (29 mg, 0.035 mmol), Ti($^i$PrO)$_4$ (58 μL, 0.21 mmol), CH$_2$Cl$_2$ (14 mL). The reaction time in this case was 18 h, while the reaction temperature was 40° C. Flash chromatography of the crude material (silica gel, 2:1 pentane-ether) afforded 59 mg (74%) of 29 as a colorless oil in 90% ee (separated by chiral GLC, Cyclosil B column, isothermal 100° C., (R)-(−)-isomer$_{rt}$=19.49 min, (S)-(+)-isomer$_{rt}$=20.31 min). [α]D=−13.9° (c 1.28, CHCl$_3$); $^1$H NMR (300 MHz): δ 1.94 (br d, 1H, J=18 Hz), 2.21–2.36 (m, 1H), 2.38–3.40 (m, 1H), 3.53–3.70 (m, 3H), 3.94–4.00 (m, 1H), 4.18 (br s, 1H), 5.54–5.56 (d, 1H, J=10 Hz), 5.90–5.95 (m,1H); $^{13}$C NMR (75.5 MHz): δ 25.2, 63.0, 64.0, 74.6, 93.2, 81.0. Anal. Calcd. for C$_6$H$_{10}$O$_2$: C, 63.14; H, 8.83. Found C, 62.91 H, 8.78.

Example 14C.

Preparation of (2-(R)-2-Methyl-5,6-dihydro-2H-pyran-2-yl)-methanol (26)

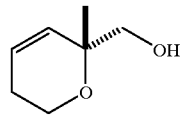

26

Following the general procedure above, the allyl ether 26 was converted into the cyclic ether 28 using the following quantities of reagents and solvents: compound 26 (100 mg, 0.64 mmol), Cl$_2$(PCy$_3$)$_2$Ru=CHPh (26 mg, 0.032 mmol), Ti($^i$PrO)$_4$ (57 μL, 0.19 mmol), CH$_2$Cl$_2$ (13 mL). The reaction time in this case was 18 h, while the reaction temperature was 40° C. Flash chromatography of the crude material (silica gel, 2:1 pentane-ether) afforded 22 mg (22%) of starting material 26 and 47 mg (57%) of 28 as a colorless oil in 90% ee (separated by chiral GLC, Cyclosil B column, isothermal 120° C., (R)-(−)-isomer, =10.08 min, (S)-(+)-isomer$_{rt}$=10.58 min). [α]D=−24.3° (c 2.07, CHCl$_3$); $^1$H NMR (300 MHz) δ 1.18 (s, 3H), 1.94–2.19 (m, 2H), 3.39 (d, 1H, J=11 Hz), 3.51 (d, 1H, J=11 Hz), 3.72–3.85 (m, 2H), 5 53 (d, 1H, J=10 Hz), 5.89–5.95 (m, 1H); $^{13}$C NMR (75.5 MHz) δ 21.5, 25.0, 59.4, 68.4, 74.5, 126.1, 131. 0. Anal. Calc'd. for C$_7$H$_{12}$O$_2$: C, 65.60; H, 9.44. Found: C, 65.45; H, 9.22.

Example 14D.

Preparation of 2-(R)2,5,6,7-tetrahydro-oxepin-2-ylmethyl acetate

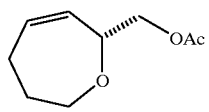

Following the general procedures above, the allyl ether 2-(R)-2-methyl-2-pent-4-enyloxy-but-3-en-1-ol (Example 13E) was acylated and then converted into the cyclic ether using the following quantities of reagents and solvents: allyl ether (93 mg, 0.47 mmol), Cl$_2$(PCy$_3$)$_2$Ru=CHPh (8 mg, 0.009 mmol), CH$_2$Cl$_2$ (9 mL). The reaction time in this case was 3 h. Flash chromatography of the crude material (silica gel, 2:1 pentane-ether) afforded 65 mg (81%) of the cyclized product as a colorless oil in 90% ee (separated by chiral GLC, Cyclosil B column, isothermal 120° C., (R)-(+)-isomer$_{rt}$=19.87 min, (S)-(−)-isomer$_{rt}$=20.49 min). [α]D=+56.1° (c 2.39, CHCl$_3$); $^1$H NMR (300 MHz) δ 1.72–1.82 (m, 2H), 2.03 (s, 3H), 2.12–2.20 (m, 1H), 2.31–2.37 (m, 1H), 3.62–3.70 (m, 1H), 3.99–4.11 (m, 3H), 4.25 (br s, 1H), 5.46 (d, 1H, J=11 Hz), 5.82–5.90 (m, 1H); $^{13}$C NMR (75.5 MHz) δ 20.8, 26.8, 28.7, 66.5, 71.3, 75.8, 129.4, 133.8, 170.9. Anal. Calc'd. for C$_9$H$_{14}$O$_3$: C, 63.51; H, 8.29. Found: C, 63.65; H, 8.40.

Example 15.

Preparation of 2-(R)-2-(2-Hydroxy-ethylamino)-2-methyl-but-3-en-1-ol

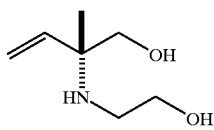

Following the general procedure of Example 1, 2-aminoethanol was reacted with isoprene monoepoxide using the following quantities of reagents and solvents: Pd$_2$dba$_3$·CHCl$_3$ (2.6 mg, 2.5 μmol), (S,S)-8 (5.2 mg, 7.5 μmol), a 1.0 M solution of Et$_3$B in THF (2.5 μL, 2.5 μmol), 2aminoethanol (15 μL, 0.25 mmol), isoprene monoepoxide (25 μL, 0.25 mmol), CH$_2$Cl$_2$ (2.5 mL). The reaction time in this case was 2 h. Flash chromatography of the crude material (silica gel, 4:1 pentane-ether) afforded ~30 mg (~80%) of the N-addition product as a colorless oil. $^1$H NMR (300 MHz) δ 1.12 (s, 3H), 2.59 (t, 2H, J=5 Hz), 3.36 (d, 1H, J=11 Hz), 3.41 (br s, 3H), 3.43 (d, 1H, J=11 Hz), 3.63 (t, 2H, J=5 Hz), 5.09 (d, 1H, J=18Hz), 5.15 (d, 1H, J=11 Hz). 5.75 (dd, 1H, J=11, 18 Hz); $^{13}$C NMR (75.5 MHz) δ 20.3, 44.0, 58.1, 61.7, 68.4, 115.0, 141.6.

Example 16.

Preparation of tert-Butyl (2-(1-(RS)-(1-Hydroxymethyl-1-phenyl-allyloxy)-ethyl))-carbamate

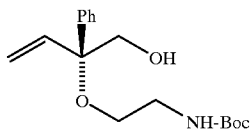

To an oven-dried sealed tube was added Pd$_2$dba$_3$·CHCl$_3$ (2.6 mg, 2.5 μmol), chiral ligand (S,S-8 (5.2 mg, 7.5 μmol), DMAP (1.5 mg, 12 μmol) and a stirbar. Three drops dry CH$_2$Cl$_2$ were added to wet the catalyst, and the tube was then placed under reduced pressure (vacuum pump) for 10 sec and refilled with At; this purging procedure was repeated five times to ensure no oxygen remained in the reaction vessel. After being placed under an Ar atmosphere, freshly distilled and degassed CH$_2$Cl$_2$ was added (2.5 mL) and the resulting dark purple mixture was stirred at room temperature until it turned a deep orange color (roughly 5 min). During this time, neat Boc-protected ethanolamine (40 mg, 0.25 mmol) and a 1.0 M solution of Et$_3$B in THF (0.25 mL, 0.25 mmol) was added. Finally, $^2$-phenyl-vinyloxirane (38 μL, 0.25 mmol) to the mixture, and the solution turned bright yellow; the tube was then sealed and heated to 40° C. Stirring was continued for 18 h, at which point the solvent was removed in vacuo. The crude product was purified by flash chromatography on silica gel (pentane-diethyl ether, 2:1), to give ~35 mg (~50%) of the O-addition product as a colorless oil. $^1$H NMR (300 MHz) 5 1.43 (s, 9H), 2.12 (br s, 1H), 3.31–3.39 (m, 4H), 3.83 (d, 1H, J=12 Hz), 3.88 (d, 1H, J=12 Hz), 5.00 (br s, 1H), 5.37 (d, 1H, J=18 Hz), 5.44 (d, 1H, J=11 Hz), 6.04 (dd, 1H, J=11, 18 Hz), 7.26–7.38 (m, 5H); $^{13}$C NMR (75.5 MHz) δ 28.4, 41.0, 62.4, 67.0, 79.3, 81.9, 118.1, 126.9, 127.7, 128.4, 137.4, 139.9, 156.1.

It is claimed:

1. A method of selectively adding a nucleophilic species to a vinylic epoxide, wherein said nucleophilic species is a nucleophilic oxygen or nitrogen species, said method comprising
contacting said epoxide with a borane or borate reagent, in the presence of said nucleophilic species and a chiral catalytic Pd complex,
thereby forming an addition product which is enriched in one of the possible stereoisomeric products of such addition.

2. The method of claim 1, wherein said nucleophilic species is a nucleophilic oxygen species.

3. The method of claim 1, wherein said nucleophilic oxygen species is selected from a primary alcohol, water, an acetate, a carbonate, and a bicarbonate.

4. The method of claim 1, wherein said borane or borate reagent comprises boron substituted with three groups independently selected from alkyl, alkoxy, aryl, aryloxy, aralkyl, aralkyloxy, alkylamino, arylamino, aralkylamino, hydroxy, and oxide.

5. The method of claim 4, wherein said borane or borate reagent is a trialkylborane, dialkylalkoxyborane, dialkoxyalkylborane, or trialkyl borate, wherein the alkyl or alkoxy substituents may be further substituted with aryl.

6. The method of claim 5, wherein said boron reagent is BR$_3$ BR$_2$OR', BR(OR')$_2$, or B(OR)$_3$, where R and R' are independently C$_1$ to C$_4$ alkyl or benzyl.

7. The method of claim 1, wherein said chiral catalytic Pd complex is formed in situ from (i) a Pd(0) species, or a Pd(II) species effective to be reduced to a Pd(0) species, and (ii) a chiral ligand effective to form said complex by reaction with said Pd(0) species.

8. The method of claim 1, wherein said chiral catalytic Pd complex includes a chiral ligand, said ligand comprising (i) a chiral component derived from a chiral diamine, diol, amino alcohol, or dicarboxylic acid, said component having first and second chiral centers, each substituted with a group X selected from oxygen, nitrogen, or a carbonyl group, and, (ii) linked to each group X, a binding component, comprising a sterically bulky group effective to complex with the palladium atom.

9. The method of claim 8, wherein said sterically bulky group is a phosphine-containing group.

10. The method of claim 9, wherein said phosphine-containing group is a (diarylphosphino)aryl binding group.

11. The method of claim 8, wherein each of said binding components is linked to said chiral center via a carboxylic amide or carboxylic ester linkage.

12. The method of claim 8, wherein said chiral centers are connected by a direct bond or by a chain of one to three atoms comprising linkages selected from alkyl alkenyl, alkyl ether, alkyl amino, or a combination thereof.

13. The method of claim 12, wherein said chiral component is derived from a chiral 1,2-diamine.

14. The method of claim 13, wherein said chiral 1,2-diamine is derived from enantiomerically enriched trans-1, 2-cyclohexyldiamine, trans-1,2-diamino-1,2-diphenylethane, or dibenzo-2,3-diamino-[2.2.2] bicyclooctane.

15. The method of claim 10, wherein each said (diarylphosphino)aryl binding group is independently selected from 2-(diphenylphosphino)benzene and 2-(diphenylphosphino) naphthalene.

16. The method of claim 1, wherein said vinylic epoxide is a terminal epoxide, having no further substitution at the epoxy carbons.

17. The method of claim 1, wherein said addition is regioselective, in that the nucleophilic species adds predominantly at the epoxy carbon of said epoxide bearing the vinylic group, giving predominantly a 1,2-addition product.

18. The method of claim 1, wherein said addition is enantioselective, producing an addition product having an enantiomeric excess greater than 75%.

19. The method of claim 18, wherein said enantiomeric excess is greater than 95%.

20. The method of claim 2, useful for producing enantiomerically enriched 1,2-diols, wherein said nucleophilic oxygen species is water, an acetate, a carbonate, or a bicarbonate, and when said nucleophilic oxygen species is an acetate, a carbonate, or a bicarbonate, said contacting takes place in the presence of water.

21. The method of claim 1, wherein said nitrogen nucleophile is an alkyl or aralkyl amine.

22. The method of claim 21, wherein said nitrogen nucleophile is an alkyl amine.

23. The method of claim 22, wherein said amine is a primary amine.

24. A method of selectively adding carbonate to a vinylic epoxide, said method comprising contacting said epoxide, in a chlorocarbon solvent, with carbon dioxide, a carbonate, or a bicarbonate, in the presence of a chiral catalytic Pd complex and water, thereby forming a cyclic carbonate product which is enriched in one of the possible stereoisomeric products of such addition.

25. The method of claim 24, wherein said vinylic epoxide is a terminal epoxide, having no further substitution at the epoxy carbons.

26. The method of claim 24, wherein said chiral catalytic Pd complex is formed in situ from (i) a Pd(0) species, or a Pd(II) species effective to be reduced to a Pd(0) species, and (ii) a chiral ligand effective to form said complex by reaction with said Pd(0) species.

27. The method of claim 24, wherein said chiral catalytic Pd complex includes a chiral ligand, said ligand comprising (i) a chiral component derived from a chiral diamine, diol, amino alcohol, or dicarboxylic acid, said component having first and second chiral centers, each substituted with a group X selected from oxygen, nitrogen, or a carbonyl group, and, (ii) linked to each group X, a binding component, comprising a sterically bulky group effective to complex with the central palladium atom.

28. The method of claim 27, wherein said sterically bulky group is a phosphine-containing group.

29. The method of claim 28, wherein said phosphine-containing group is a (diarylphosphino)aryl binding group.

30. The method of claim 27, wherein said chiral centers are connected by a direct bond or by a chain of one to three atoms comprising linkages selected from alkyl, alkenyl, alkyl ether, alkyl amino, or a combination thereof.

31. The method of claim 30, wherein said chiral component is derived from a chiral 1,2-diamine.

* * * * *